US005962327A

United States Patent [19]

Dujon et al.

[11] Patent Number: 5,962,327
[45] Date of Patent: Oct. 5, 1999

[54] NUCLEOTIDE SEQUENCE ENCODING THE ENZYME I-SCEI AND THE USES THEREOF

[75] Inventors: Bernard Dujon, Gif sur Yvette; Andre Choulika, Paris, both of France; Laurence Colleaux, Edinburgh, United Kingdom; Cecile Fairhead, Malakoff; Arnaud Perrin, Paris, both of France; Anne Plessis; Agnes Thierry, both of Paris, France

[73] Assignee: Institut Pasteur Universite Paris-VI, Paris, France

[21] Appl. No.: 08/417,226

[22] Filed: Apr. 5, 1995

Related U.S. Application Data

[60] Division of application No. 07/971,160, Nov. 5, 1992, Pat. No. 5,474,896, which is a continuation-in-part of application No. 07/879,689, May 5, 1992, abandoned.

[51] Int. Cl.$^6$ .................................................. C12N 15/55
[52] U.S. Cl. ....................... 435/478; 435/320.1; 536/23.2
[58] Field of Search .............................. 435/320.1, 122.3, 435/478; 536/23.2

[56] References Cited

PUBLICATIONS

Dujon, B., Sequence of the Intron and Flanking Exons of the Mitochondrial 21s rDNA Gene of Yeast Strains Having Different Alleles at the ω and rib–1 Loci, Cell, vol. 20: 185–197 (1980).

Michel, F. et al., Comparison of Fungal mitochondrial introns reveals extensive homologies in RNA secondary structure, Biochimie, vol. 64: 867–881 (1982).

Michel, F. and Dujon, B., Conservation of RNA secondary structures in two intron families including mitochondrial–, chloroplast–and nuclear–encoded members, EMBO Journal, vol. 2(1) : 33–38 (1983).

Jacquier, A. and Dujon, B., the Intron of the Mitochondrial 21s rRNA Gene: Distribution in Different Yeast Species and Sequence Comparison Between *Kluyveromyces thermotolerans* and *Saccharomyces cerevisiae*, Mol. Gen. Genet., 192: 487–499 (1983).

Dujon, B. and Jacquier, A., Mitochondria 1983, Walter de Gruyter & Co., pp. 389–403.

Jacquier, A. and Dujon, B., An Intron–Encoded Protein is Active in a Gene Conversion Process That Spreads an Intron into a Mitochondrial Gene, Cell, vol. 41: 383–394 (1985).

Dujon, B. et al., in Achievements and Perspectives of Mitochondrial Research, vol. II: Biogenesis, Elsevier Science Publishers, pp. 215–225 (1985).

Colleaux, L. et al., Universal Code Equivalent of Yeast Mitochondrial Intron Reading Frame is Expressed into E. Coli as a Specific Double Strand Endonuclease, Cell, vol. 44: 521–533 (1986).

Michel, F. and Dujon, B., Genetic Exchanges between Bacteriophage T4 and Filamentous Fungi?, Cell, vol. 46: 323 (1986).

Colleaux, L. et al., Recognition and cleavage site of the intron–encoded omega transposase, Proc. Natl. Acad. Sci. USA, vol. 85: 6022–6026 (1988).

Dujon, B., Group I introns as mobile genetic elements: facts and mechanistic speculations—a review, Gene, vol. 82: 91–114 (1989).

Dujon, B. et al., Mobile introns: definition of terms and recommended nomenclature, Gene, vol. 82: 115–118 (1989).

Monteilhet, C. et al., Purification and characterization of the in vitro activity of I–SceI, a novel and highly specific endonuclease encoded by a group 1 intron, Nucleic Acids Research , vol. 18(6), 1407–1413 (1990).

Colleaux, L. et al., The apocytochrome b gene of *Chalamydomonas smithii* contains a mobile intron related to both *Saccharomyces* and *Neurospora* introns, Mol. Gen. Genet., vol. 223: 288–296 (1990).

Dujon, B. et al., in Extrachromosomal Elements in Lower Eukaryotes, (Plenum Publishing Corporation 1986), pp. 5–27.

Thierry, A. et al., Cleavage of yeast and bacteriophage T7 genomes at a single site using the rare cutter endonuclease I–SceI, Nucleic Acids Research, vol. 19(1): 189–190 (1991).

Plessis, A. et al., Site–specific recombination by I–SceI; a mitochondrial group I intron–encoded endonuclease expressed in the yeast nucleus, Genetics, vol. 130(3): 451–460 (1992).

Tartof et al., "New cloning vectors and techniques . . ." Gene 67:169–182 (1988).

Colleaux et al., "Rapid Physical Mapping of YAC inserts . . . ," Human Mol. Genet., 2(3) :265–271 (1993).

Dujon, B. et al., "Mobile Introns," Abstract presented at EMBO Workshop, Roscoff, France, Jun. 24–28, 1990.

Sharp, P. M., et al., (1988) Nucl. Acids Res. 16(17) 8207–8211.

Sharp, P.M., et al. (1987) Nucl. Acids. Res. 15(3) 1281–1295.

Gouy, M, et al. (1982) Nucl. Acids Res. 10, 7055–7074.

*Primary Examiner*—Charles L. Patterson, Jr.
*Attorney, Agent, or Firm*—Finnegan, Henderson, Farabow, Garrett, & Dunner, L.L.P.

[57] ABSTRACT

An isolated DNA encoding the enzyme I-SceI is provided. The DNA sequence can be incorporated in cloning and expression vectors, transformed cell lines and transgenic animals. The vectors are useful in gene mapping and site-directed insertion of genes.

29 Claims, 24 Drawing Sheets

FIG. 1

```
AAAAATAAAATCAT ATG AAA AAT ATT AAA AAT CAA GTA ATC AAT CTC GGT CCT AAT TCT
                M   K   N   I   K   N   Q   V   I   N   L   G   P   N   S

AAA TTA AAA GAA TAT AAA TCA CAA TTA ATT GAA TTT GAA CAA TTT GAA GCA
 K   L   K   E   Y   K   S   Q   L   I   E   F   E   Q   F   E   A

GGT ATT TTA ATT GGA GAT GCT TAT GCT CGT AGT GAT ATT GAA GGT AAA ACT TAT
 G   I   L   I   G   D   A   Y   A   R   S   D   I   E   G   K   T   Y

TGT ATG CAA TTT CAC TCC AAA TCC AAT AAG GCA ATG TAC AGT GAT CAT CGT GTA GTA TAT GAT
 C   M   Q   F   H   S   K   S   N   K   A   M   Y   S   D   H   R   V   V   Y   D

CAA GTA TTA TCA CCT CCT CAT AAA CAT AAA GAA GAA AGA GAT CAT AAA GTT TTA TTA
 Q   V   L   S   P   P   H   K   H   K   E   E   R   D   H   K   V   L   L

ATT ACC TGG GGA GCT CAA ACT TTT AAA AAA CAT CAA AAT AAT TTT GCT AAC TTA
 I   T   W   G   A   Q   T   F   K   K   H   Q   N   N   F   A   N   L

ATT GTA AAT AAT AAA CTT ATT CCT GAT GAT CAA TTA AAT AAT ATT TAT ACA CCT ATG
 I   V   N   N   K   L   I   P   D   D   Q   L   N   N   I   Y   T   P   M

AGT CTG GCA TAT TGG TTT ATG GAT GGG AGT TTT AAA GGT TAT GAA ACT TCT CTT
 S   L   A   Y   W   F   M   D   G   S   F   K   G   Y   E   T   S   L

AAT AAT GTA AAT AAA TTA AAT AAT AGT TTT AAA AAT TAT GAA AAA ATT ATT CTT GTA
 N   N   V   N   K   L   N   N   S   F   K   N   Y   E   K   I   I   L   V

AAA GGT ATT TAT TAT GAT TCT AGT AAT TAT ATT TAT TAT TTT AAT AAT AAT AAA AAA CCA
 K   G   I   Y   Y   D   S   S   N   Y   I   Y   Y   F   N   N   N   K   K   P

ATT TAT ATT AGA ATT CTG AGT TAT AAA AAT GTA TTT AAT CCT TAT TTA CCT TAT TTA
 I   Y   I   R   I   L   S   Y   K   N   V   F   N   P   Y   L   P   Y   L

ATT CCT CAA ATG ATG TAT AAA CTG CCT AAT ACT TCA GAA ACT TTT TTA AAA TAA
 I   P   Q   M   M   Y   K   L   P   N   T   S   E   T   F   L   K   *
```

```
Bam HI
 |
CCGGATCCATG CAT ATG AAA AAC ATC AAA AAA AAC CAG GTA AAC ATG AAC CTG GGT CCG AAC TCT
            H   M   K   N   I   K   K   N   Q   V   N   M   N   L   G   P   N   S

1. AAA CTG CTG AAA GAA TAC AAA TCC CAG CTG TAC CAG ATG AAC CTG GAA CAG TTC GAA GCA
   K   L   L   K   E   Y   K   S   Q   L   Y   Q   M   N   L   E   Q   F   E   A

GGT ACT GGT CTG ATC CTG GGT |GAT| GCT TAC GCA AAA AAC AAA CTG GAT TTC AAA ACC TAC
   G   T   G   L   I   L   G    D   A   Y   A   K   N   K   L   D   F   K   T   Y

TGT ATG CAG TTC GAG TCC CCG CAG ACT ATC CGT ATG GAC GTA CAC AAC GTA TGT CTG CTG GAT
   C   M   Q   F   E   S   P   Q   T   I   R   M   D   V   H   N   V   C   L   L   D

CAG TGG GTA CTG GGC GCC CAG AAA AAA AAA CAC GAA CGT GTT GCT CAA CAC AAC GGT CTG GTA
   Q   W   V   L   G   A   Q   K   K   K   H   E   R   V   A   Q   H   N   G   L   V

ATC ACC TGG AAC AAC CAG AAA AAA CCG ACT TTC ATC ACC AAA CAA CTG TAC AAC CTG CTG TTC
   I   T   W   N   N   Q   K   K   P   T   F   I   T   K   Q   L   Y   N   L   L   F

ATC GTT AAC AAC ATG AAC CCG ATG AAC GAT GAA GAA TAC AAC CTG ATC AAC CGG ATG
   I   V   N   N   M   N   P   M   N   D   E   E   Y   N   L   I   N   P   M

2. TCT CTG GCA TAC TGG TTC ATG |GAT GGT| ACC CAG AAA TGG GAT TTC GAA GAA GTA AAC TCT ACC
   S   L   A   Y   W   F   M    D   G    T   Q   K   W   D   F   E   E   V   N   S   T

AAC AAA TCG ATC GTA CTG AAA AAC TTC CAA CTG TAC ACT TGT AAC CTA TAC TTC ATC ATT CTG GTT
   N   K   S   I   V   L   K   N   F   Q   L   Y   T   C   N   L   Y   F   I   I   L   V

AAG GGT CTG CGT AAC GCC AAA TCT ATG TCT TAT ATC TTC ATC AAC AAA CCG AAA AAA CCG
   K   G   L   R   N   A   K   S   M   S   Y   I   F   I   N   K   P   K   K   P

ATC ATC TAC ATC GAT ATG ATG TAC AAA TAC AAC CCG CCG AAC ACT TCC TCC GAA ACT TTC CTG AAA TAA
   I   I   Y   I   D   M   M   Y   K   Y   N   P   P   N   T   S   S   E   T   F   L   K   *

TAAGTCGACTGCAGGATCCGGTAAGTAAGTAA
   |   |    |
  SalI PstI BamHI 1 and 2: THESE AMINO ACIDS ARE ABSOLUTELY NECESSARY TO PRODUCE CATALYTIC
         ACTIVITY, OTHER SUBSTITUTIONS ARE POSSIBLE, SUCH AS DELETIONS
         OF THE 10 FIRST AMINO ACIDS.
```

```
1667 GCGGACAGGTATCCGGTAAGCGGCAGGGTCGGAACAGGAGAGCGCACGAGGAGCTTCCAGGGGAAACGCCTGGTATCT 1746

1747 TTATAGTCCTGTCGGGTTTCGCCACCTCTGACTTGAGCGTCGATTTTTGTG ATG CTC GTC AGG GGG GCG GAG 1818
                                                          M   L   V   R   G   A   E   7

1819 CCT ATG GAA AAA CGC CAG CAA CGC GGC CTT TTT ACG GTT CCT GGC CTT TTG CTG GCC TTT 1878
      P   M   E   K   R   Q   Q   R   G   L   F   T   V   P   G   L   L   A   F   27

1879 TGC TCA CAT CTT TCC TGC GTT ATC CCC TGA TTCTGTGGATAACCGTATTACCGCCTTTGAGTGAGC 1947
      C   S   H   L   S   C   V   I   P   *                                        38

1948 TGATACCGCTCGCCGCCGAACGACCGAGCGCAGCGAGTGAGCGGAAGAGCGCCCAATACGCAAAC 2027

2028 CGCCTCTCCCCGGGTTGGCCGATTCATTA ATG CAG CTG GCA CGA CAG GTT TCC CGA CTG GAA AGC 2094
                                     M   Q   L   A   R   Q   V   S   R   L   E   S   12

2095 GGG CAG TGA GCGCAACGCAATTA ATG TGA GTTAGCTCACTCATTAGGCACCCCAGGCTTTACACTTT ATG 2164
      G   Q   *                   M   *                                            M  1

2165 CTT CCG GCT CGT ATG TTG TGT GGA ATT GTG AGC GGA TAA CAATTTCACACAGGAAACAGCT ATG 2228
      L   P   A   R   M   L   C   G   I   V   S   G   *                            M  1

2229 ACC ATG ATT ACG AAT TCT CAT GTT TGA CAGCTTATCATCGATAAGCTTTA ATG CGG TAG TTTATCAC 2295
      T   M   I   T   N   S   H   V   *                          M   R   *         3

2296 AGTTAAATTGCTAACGCAGTCAGGCACCGTGT ATG AAA TCT AAC AAT GCG CTC ATC GTC ATC CTC GGC 2363
                                       M   K   S   N   N   A   L   I   V   I   L   G   12

2364 ACC GTC ACC CTG GAT GCT GTA GGC ATA GGC TTG GTT ATG CCG GTA CTG CCG GGC CTC TTG 2423
      T   V   T   L   D   A   V   G   I   G   L   V   M   P   V   L   P   G   L   L   32

2424 CGG GAT ATC CGC CTG ATG CGT GAA CGT GAC CGC AAC CAC CGT GAC ATG TGT GTG CTG 2483
      R   D   I   R   L   M   R   E   R   D   R   N   H   R   D   M   C   V   L   52

2484 TTC CGC TGG GCA TGC CAG GAC AAC TTC TGG TCC GGT AAC GTG CTG AGC CCG GCC AAG CTT 2543
      F   R   W   A   C   Q   D   N   F   W   S   G   N   V   L   S   P   A   K   L   72
```

Positions that can be changed without affecting enzyme activity (demonstrated)
positions -1 and -2 are not natural. The two amino acids are added due to cloning strategies positions 1 to 10: can be deleted
position 36: G is tolerated
position 40: M or V are tolerated
position 41: S or N are tolerated
position 43: A is tolerated
position 46: V or N are tolerated
position 91: A is tolerated
positions 123 and 156: L are tolerated
position 223: A and S are tolerated Changes that affect enzyme activity (demonstrated)

position 19: L to S
position 38: I to S or N
position 39: G to D or R
position 40: L to Q
position 42: L to R
position 44: D to E G or H
position 45: A to E or D
position 46: Y to D
position 47: I to R or N
position 80: L to S
position 144: D to E
position 145: D to E
position 146: G to E
position 147: G to S

FIG. 5

Group I Intron Encoded Endonucleases and Related Endonucleases

| | ENDONUCLEASE | RECOGNITION SEQUENCE / CLEAVAGE SITE / ▽ INTRON SITE |
|---|---|---|
| TWO DODECAPEPTIDE FAMILY (OR 4 BP CUTTERS) | I-Sce I (Saccharomyces mitochondria) | CGC\|TAGGGA▽TAA\|CAGGGTAAT\|ATAGC<br>GCG\|ATCCCTATTGTCCCATTA\|TATCG |
| | I-Sce IV (Saccharomyces mitochondria) | TTCTCATGATT▽A\|GCTCTAATCCATGG<br>AAGAGTAC\|TAATCGAGATTAGGTACC |
| | I-Sce II (Saccharomyces mitochondria) | C\|TTTGGT▽CATCC\|AGAAGTA\|TATATTT<br>G\|AAACCAG\|TAGGTCTTCAT\|ATATAAA |
| | I-Ceu I (Chlamydomonas chloroplast) | TAACGGT▽CCTAA\|GGTAGCGAAATTCA<br>ATTGCCAG\|GATTCCATCGCTTTAAGT |
| | I-Ppo I (Physarum nucleus) | TG\|ACTCTC\|TTAA▽\|GGTAGCC\|AAATGCC<br>AC\|TGAGAG\|AATTCCATCGG\|TTTACGG |
| | I-Sce III (Saccharomyces mitochondria) | GGAGGTTTTGGT▽AACTATTTATTACC<br>CCTCCAAAACCATTGATAAATAATGG |
| | I-Cre I (Chlamydomonas chloroplast) | GGGTTCAAAACGT▽CGTGAGACAGTTT<br>CCCAAGTTTTGCAGCACTCTGTCAAA |
| | Endo. Sce I(RF3) (Saccharomyces mitochondria) (Non intronic) | GATGCTGTAGGC\|ATAGGCTTGGTTAT<br>CTACGACA\|TCCGTATCCGAACCAATA |
| | HO (Saccharomyces nucleus) (Non intronic) | C\|TTTCCGCAACA\|GT\|ATAATTTTATAA<br>G\|AAAGGCG\|TTGTCA\|TATTAAAATATT |
| | I-Csm I (Chlamydomonas mitochondria) (Putative endonuclease) | ACCATGGGGT▽CAAATGTCTTTCTGGG<br>TGGTACCCCAGTTTACAGAAAGACCC |
| | I-Pan I (Podospora mitochondria) (Putative endonuclease) | GTGCCTGAATGATA▽TTTATTACCTTT<br>CACGGACTTACTATAAATAATGGAAA |
| OTHER STRUCTURAL FAMILIES | I Tev I (Bacteriophage T4) | \|CAAC\|GCTCAGTAGATGTTTTCTTGGGT▽CTACCGTTTAAT<br>GT\|TG\|CGAGTCATCTACAAAAGAACCCAGATGGCAAATTA |
| | I Tev II | CAAGCTTATGAGTA▽TGAAGTGAACACGT\|TATT<br>GTTCGAATACTCATACTTCACTTGTG\|CAATAA |
| | I Tev III | GCTATTCGTTTT\|TAT GTATCTTTTGC▽GTGTAGCTTTAA<br>CGATAAGCAAAAAT\|ACATAGAAAACGCACATCGAAATT |

FIG. 6

```
                                    Sau3A I
                                     Mbo I
                                     Dpn II
                                  ScrF I
                                  Nci I
                                  Msp I
                                  Hpa II
                                  Dsa V
                                  BstK I
                                  Xma I
                                  Sma I
                                  ScrF I
                                  Nci I
                                  Dsa V
                           Rsa I      Dpn I
                           Nla IV    Nla IV
                  Sac I    Csp6 I    Alw I
                  HgiA I   BstK I                   Taq I
                  Ec1136 I BsaJ I                   Sal I
         Sph I    Rma I    Kpn I     BstY I         Hinc II
         NspC I   Bsp1286 I          Bcn I  Sfe I
  EcoR I          Xba I    Ban I     BamH I  Acc I        I-Sce I
  Apo I  Nla III  Ban II   Bcn I     Sfc I             Rma I
  Taq I  Nsp7524 I  Alu I  Ava I     Pst I   Hga I
  Alu I  Nsp I   Bfa I  Asp718  Alw I  BspW I    Bfa I              EcoR V
   | | |   | |    | |   | | | |  | |    | | | |    | |                |
  CCAAGCTCGAATTCGCATGCTCTAGAGCTCGGTACCCGGGATCCTGCAGTCGACGCTAGGGATAACAGGGTAATACAGAT   2320
  GGTTCGAGCTTAAGCGTACGAGATCTCGAGCCATGGGCCCTAGGACGTCAGCTGCGATCCCTATTGTCCCATTATGTCTA
   | | |·  | |  ·| |   ·| | | |  ·| | | |  | | |   | |·     ·      |·
  2244    2255   2262   2271   2279   2286      2296              2318
     2247   2255    2266   2275   2284     2292
       2249  2256   2265   2275    2284         2296
          2249        2261  2271   2279   2289     2297
                2255       2265    2276  2284
                  2255   2262   2271   2279     2289
                           2265    2275          2289
                           2265    2275          2290
                           2265  2272    2280
                                 2271   2279
                                   2272   2280
                                   2275
                                   2275
                                   2275
                                   2275
                                   2275
                                   2275
                                    2276
                                    2276
                                    2276
                                    2276
                                    2276
                                    2276
                                        2280
                                        2280
                                        2280
```

Construction: pGP 704 from De Lorenzo, with transposase gene and insertion of the linker[I-SceI] in NotI unique site Construction: pD 123, from J.D. Boeke
with insertion of a linker[I-SceI-NotI] in BamHI

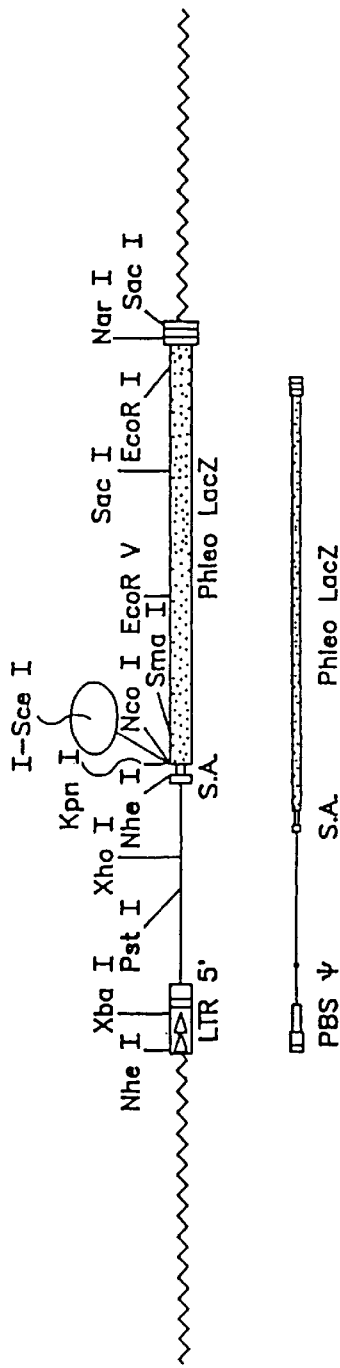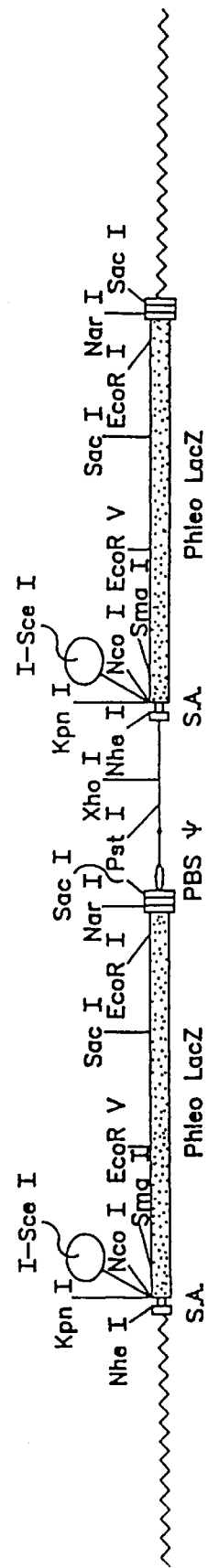
FIG. 13B
FIG. 13C

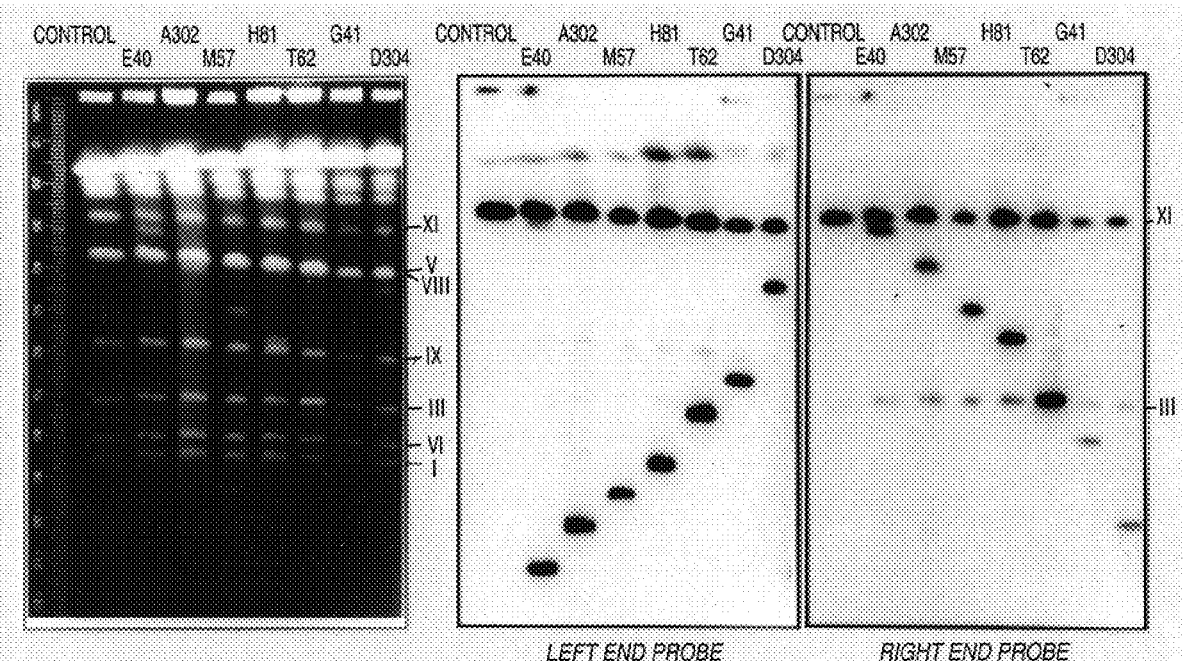

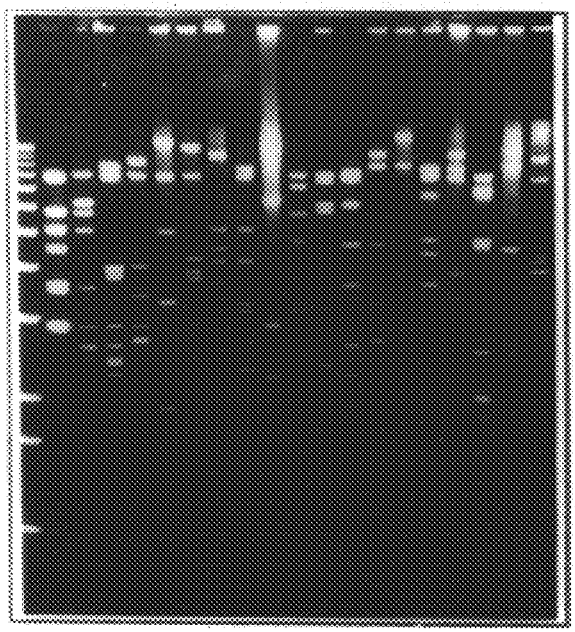
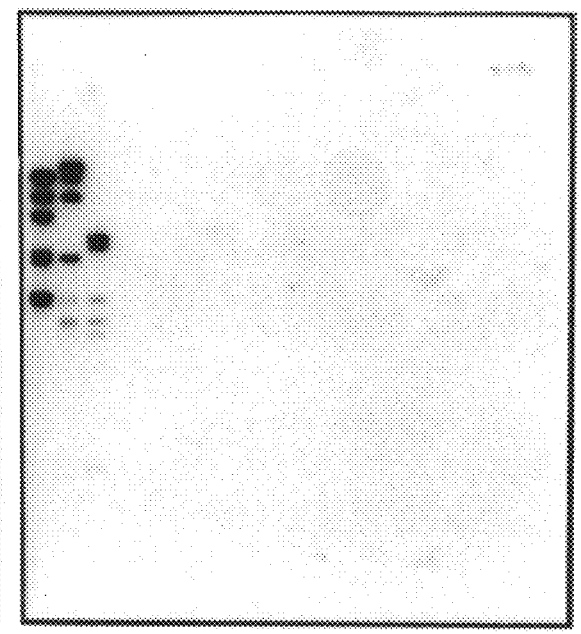
FIG. 17A                    FIG. 17B

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
      (A) LENGTH: 714 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGCATATGA AAAACATCAA AAAAAACCAG GTAATGAACC TCGGTCCGAA CTCTAAACTG      60

CTGAAAGAAT ACAAATCCCA GCTGATCGAA CTGAACATCG AACAGTTCGA AGCAGGTATC     120

GGTCTGATCC TGGGTGATGC TTACATCCGT TCTCGTGATG AAGGTAAAAC CTACTGTATG     180

CAGTTCGAGT GGAAAAACAA AGCATACATG GACCACGTAT GTCTGCTGTA CGATCAGTGG     240

GTACTGTCCC CGCCGCACAA AAAAGAACGT GTTAACCACC TGGGTAACCT GGTAATCACC     300

TGGGGCGCCC AGACTTTCAA ACACCAAGCT TTCAACAAAC TGGCTAACCT GTTCATCGTT     360

AACAACAAAA AAACCATCCC GAACAACCTG GTTGAAAACT ACCTGACCCC GATGTCTCTG     420

GCATACTGGT TCATGGATGA TGGTGGTAAA TGGGATTACA ACAAAAACTC TACCAACAAA     480

TCGATCGTAC TGAACACCCA GTCTTTCACT TTCGAAGAAG TAGAATACCT GGTTAAGGGT     540

CTGCGTAACA AATTCCAACT GAACTGTTAC GTAAAAATCA ACAAAAACAA ACCGATCATC     600

TACATCGATT CTATGTCTTA CCTGATCTTC TACAACCTGA TCAAACCGTA CCTGATCCCG     660

CAGATGATGT ACAAACTGCC GAACACTATC TCCTCCGAAA CTTTCCTGAA ATAA          714
```

(2) INFORMATION FOR SEQ ID NO:2:

(i) SEQUENCE CHARACTERISTICS:
      (A) LENGTH: 237 amino acids
      (B) TYPE: amino acid
      (D) TOPOLOGY: linear (ii) MOLECULE TYPE: peptide (xi) SEQUENCE DESCRIPTION: SEQ ID NO:2:

```
Met His Met Lys Asn Ile Lys Lys Asn Gln Val Met Asn Leu Gly Pro
  1               5                  10                  15
```

```
Asn Ser Lys Leu Leu Lys Glu Tyr Lys Ser Gln Leu Ile Glu Leu Asn
         20                  25                  30

Ile Glu Gln Phe Glu Ala Gly Ile Gly Leu Ile Leu Gly Asp Ala Tyr
             35                  40                  45

Ile Arg Ser Arg Asp Glu Gly Lys Thr Tyr Cys Met Gln Phe Glu Trp
 50                  55                  60

Lys Asn Lys Ala Tyr Met Asp His Val Cys Leu Leu Tyr Asp Gln Trp
 65                  70                  75                  80

Val Leu Ser Pro Pro His Lys Lys Glu Arg Val Asn His Leu Gly Asn
             85                  90                  95

Leu Val Ile Thr Trp Gly Ala Gln Thr Phe Lys His Gln Ala Phe Asn
             100                 105                 110

Lys Leu Ala Asn Leu Phe Ile Val Asn Lys Lys Thr Ile Pro Asn
             115                 120                 125

Asn Leu Val Glu Asn Tyr Leu Thr Pro Met Ser Leu Ala Tyr Trp Phe
 130                 135                 140

Met Asp Asp Gly Gly Lys Trp Asp Tyr Asn Lys Asn Ser Thr Asn Lys
 145                 150                 155                 160

Ser Ile Val Leu Asn Thr Gln Ser Phe Thr Phe Glu Glu Val Glu Tyr
             165                 170                 175

Leu Val Lys Gly Leu Arg Asn Lys Phe Gln Leu Asn Cys Tyr Val Lys
             180                 185                 190

Ile Asn Lys Asn Lys Pro Ile Ile Tyr Ile Asp Ser Met Ser Tyr Leu
             195                 200                 205

Ile Phe Tyr Asn Leu Ile Lys Pro Tyr Leu Ile Pro Gln Met Met Tyr
 210                 215                 220

Lys Leu Pro Asn Thr Ile Ser Ser Glu Thr Phe Leu Lys
225                 230                 235
```

(2) INFORMATION FOR SEQ ID NO:3:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
AAAAATAAAA TCATATGAAA AATATTAAAA AAAATCAAGT AATCAATCTC GGTCCTATTT      60

CTAAATTATT AAAAGAATAT AAATCACAAT TAATTGAATT AAATATTGAA CAATTTGAAG     120

CAGGTATTGG TTTAATTTTA GGAGATGCTT ATATTCGTAG TCGTGATGAA GGTAAAACTT     180

ATTGTATGCA ATTTGAGTGG AAAAATAAGG CATACATGGA TCATGTATGT TTATTATATG     240

ATCAATGGGT ATTATCACCT CCTCATAAAA AGAAAGAGT TAATCATTTA GGTAATTTAG      300

TAATTACCTG GGGAGCTCAA ACTTTTAAAC ATCAAGCTTT TAATAAATTA GCTAACTTAT     360

TTATTGTAAA TAATAAAAAA CTTATTCCTA ATAATTTAGT TGAAAATTAT TTAACACCTA     420

TGAGTCTGGC ATATTGGTTT ATGGATGATG GAGGTAAATG GGATTATAAT AAAAATTCTC     480

TTAATAAAAG TATTGTATTA AATACACAAA GTTTTACTTT TGAAGAAGTA GAATATTTAC     540

TTAAAGGTTT AAGAAATAAA TTTCAATTAA ATTGTTATGT TAAAATTAAT AAAAATAAAC     600

CAATTATTTA TATTGATTCT ATGAGTTATC TGATTTTTTA TAATTTAATT AAACCTTATT     660

TAATTCCTCA AATGATGTAT AAACTGCCTA ATACTATTTC ATCCGAAACT TTTTTAAAAT     720

AA                                                                   722
```

(2) INFORMATION FOR SEQ ID NO:4:

(i) SEQUENCE CHARACTERISTICS:
        (A) LENGTH: 235 amino acids
        (B) TYPE: amino acid
        (D) TOPOLOGY: linear (ii) MOLECULE TYPE: peptide (xi) SEQUENCE DESCRIPTION: SEQ ID NO:4:

```
Met Lys Asn Ile Lys Lys Asn Gln Val Met Asn Leu Gly Pro Asn Ser
 1               5                  10                  15

Lys Leu Leu Lys Glu Tyr Lys Ser Gln Leu Ile Glu Leu Asn Ile Glu
            20                  25                  30

Gln Phe Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
 50                  55                  60

Lys Ala Tyr Met Asp His Val Cys Leu Leu Tyr Asp Gln Trp Val Leu
 65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Leu Ile Pro Asn Asn Leu
        115                 120                 125

Val Glu Asn Tyr Leu Thr Pro Met Ser Leu Ala Tyr Trp Phe Met Asp
    130                 135                 140

Asp Gly Gly Lys Trp Asp Tyr Asn Lys Asn Ser Leu Asn Lys Ser Ile
145                 150                 155                 160

Val Leu Asn Thr Gln Ser Phe Thr Phe Glu Glu Val Cys Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Ile Ile Lys Pro Tyr Leu Ile Pro Gln Met Met Tyr Lys Leu
    210                 215                 220

Pro Asn Thr Ile Ser Ser Glu Thr Phe Leu Lys
225                 230                 235
```

(2) INFORMATION FOR SEQ ID NO:5:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CCGGATCCAT GCATATGAAA AACATCAAAA AAAACCAGGT AATGAACCTG GGTCCGAACT      60

CTAAACTGCT GAAAGAATAC AAATCCCAGC TGATCGAACT GAACATCGAA CAGTTCGAAG     120

CAGGTATCGG TCTGATCCTG GGTGATGCTT ACATCCGTTC TCGTGATGAA GGTAAAACCT     180

ACTGTATGCA GTTCGAGTGG AAAAACAAAG CATACATGGA CCACGTATGT CTGCTGTACG     240

ATCAGTGGGT ACTGTCCCCG CCGCACAAAA AACAACGTGT TAACCACCTG GGTAACCTGG     300
```

```
TAATCACCTG GGGCGCCCAG ACTTTCAAAC ACCAAGCTTT CAACAAACTG GCTAACCTGT      360

TCATCGTTAA CAACAAAAAA ACCATCCCGA ACAACCTGGT TGAAAACTAC CTGACCCCGA      420

TGTCTCTGGC ATACTGGTTC ATGGATGATG GTGGTAAATG GGATTACAAC AAAAACTCTA      480

CCAACAAATC GATCGTACTG AACACCCAGT CTTTCACTTT CGAAGAAGTA GAATACCTGG      540

TTAAGGGTCT GCGTAACAAA TTCCAACTGA ACTGTTACGT AAAAATCAAC AAAAACAAAC      600

CGATCATCTA CATCGATTCT ATGTCTTACC TGATCTTCTA CAACCTGATC AAACCGTACC      660

TGATCCCGCA GATGATGTAC AAACTGCCGA ACACTATCTC CTCCGAAACT TTCCTGAAAT      720

AATAAGTCGA CTGCAGGATC CGGTAAGTAA GTAA                                  754
```

(2) INFORMATION FOR SEQ ID NO:6:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AATGCTTTCC A                                                            11
```

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GTTACGCTAG GGATAACAGG GTAAT                                             25
```

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CAATGCGATC CCTATTGTCC CATTA                                             25
```

(2) INFORMATION FOR SEQ ID NO:9:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GCGGACAGGT ATCCGGTAAG CGGCAGGGTC GGAACAGGAG AGCGCACGAG GGAGCTTCCA       60

GGGGGAAACG CCTGGTATCT TTATAGTCCT GTCGGGTTTC GCCACCTCTG ACTTGAGCGT      120

CGATTTTTGT GATGCTCGTC AGGGGGGCGG AGCCTATGGA AAAACGCCAG CAACGCGGCC      180
```

-continued

```
TTTTTACGGT TCCTGGCCTT TTGCTGGCCT TTTGCTCACA TGTTCTTTCC TGCGTTATCC      240

CCTGATTCTG TGGATAACCG TATTACCGCC TTTGAGTGAG CTGATACCGC TCGCCGCAGC      300

CGAACGACCG AGCGCAGCGA GTCAGTGAGC GAGGAAGCGG AAGAGCGCCC AATACGCAAA      360

CCGCCTCTCC CCGCGCGTTG GCCGATTCAT TAATGCAGCT GGCACGACAG GTTTCCCGAC      420

TGGAAAGCGG GCAGTGAGCG CAACGCAATT AATGTGAGTT AGCTCACTCA TTAGGCACCC      480

CAGGCTTTAC ACTTTATGCT TCCGGCTCGT ATGTTGTGTG GAATTGTGAG CGGATAACAA      540

TTTCACACAG GAAACAGCTA TGACCATGAT TACGAATTCT CATGTTTGAC AGCTTATCAT      600

CGATAAGCTT TAATGCGGTA GTTTATCACA GTTAAATTGC TAACGCAGTC AGGCACCGTG      660

TATGAAATCT AACAATGCGC TCATCGTCAT CCTCGGCACC GTCACCCTGG ATGCTGTAGG      720

CATAGGCTTG GTTATGCCGG TACTGCCGGG CCTCTTGCGG GATATCCGCC TGATGCGTGA      780

ACGTGACGGA CGTAACCACC GCGACATGTG TGTGCTGTTC CGCTGGGCAT GCCAGGACAA      840

CTTCTGGTCC GGTAACGTGC TGAGCCCGGC CAAGCTTACT CCCCATCCCC CTGTTGACAA      900

TTAATCATCG GCTCGTATAA TGTGTGGAAT TGTGAGCGGA TAACAATTTC ACACAGGAAA      960

CAGGATCCAT GCATATGAAA AACATCAAAA AAAACCAGGT AATGAACCTG GGTCCGAACT     1020

CTAAACTGCT GAAAGAATAC AAATCCCAGC TGATCGAACT GAACATCGAA CAGTTCGAAG     1080

CAGGTATCGG TCTGATCCTG GGTGATGCTT ACATCCGTTC TCGTGATGAA GGTAAAACCT     1140

ACTGTATGCA GTTCGAGTGG AAAAACAAAG CATACATGGA CCACGTATGT CTGCTGTACG     1200

ATCAGTGGGT ACTGTCCCCG CCGCACAAAA AGAACGTGT TAACCACCTG GGTAACCTGG     1260

TAATCACCTG GGGCGCCCAG ACTTTCAAAC ACCAAGCTTT CAACAAACTG GCTAACCTGT     1320

TCATCGTTAA CAACAAAAAA ACCATCCCGA ACAACCTGGT TGAAAACTAC CTGACCCCGA     1380

TGTCTCTGGC ATACTGGTTC ATGGATGATG GTGGTAAATG GGATTACAAC AAAAACTCTA     1440

CCAACAAATC GATCGTACTG AACACCCAGT CTTTCACTTT CGAAGAAGTA GAATACCTGG     1500

TTAAGGGTCT GCGTAACAAA TTCCAACTGA ACTGTTACGT AAAAATCAAC AAAAACAAAC     1560

CGATCATCTA CATCGATTCT ATGTCTTACC TGATCTTCTA CAACCTGATC AAACCGTACC     1620

TCATCCCCCA GATGATGTAC AAACTGCCGA ACACTATCTC CTCCGAAACT TTCCTGAAAT     1680

AATAAGTCGA CCTGCAGCCC AAGCTTGGCA CTGGCCGTCG TTTTACAACG TCGTGACT        1738
```

(2) INFORMATION FOR SEQ ID NO:10:

(i) SEQUENCE CHARACTERISTICS:
      (A) LENGTH: 37 amino acids
      (B) TYPE: amino acid
      (D) TOPOLOGY: linear (ii) MOLECULE TYPE: peptide (xi) SEQUENCE DESCRIPTION: SEQ ID NO:10:

```
Met Leu Val Arg Gly Ala Glu Pro Met Glu Lys Arg Gln Gln Arg Gly
 1               5                  10                  15

Leu Phe Thr Val Pro Gly Leu Leu Ala Phe Cys Ser His Val Leu
            20                  25                  30

Ser Cys Val Ile Pro
        35
```

(2) INFORMATION FOR SEQ ID NO:11:

(i) SEQUENCE CHARACTERISTICS:
      (A) LENGTH: 14 amino acids
      (B) TYPE: amino acid (D) TOPOLOGY: linear (ii) MOLECULE TYPE: peptide (xi) SEQUENCE DESCRIPTION: SEQ ID NO:11:

Met Gln Leu Ala Arg Gln Val Ser Arg Leu Glu Ser Gly Gln
    1               5                   10

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:12:

Met Leu Pro Ala Arg Met Leu Cys Gly Ile Val Ser Gly
    1               5                   10

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

Met Thr Met Ile Thr Asn Ser His Val
    1               5

(2) INFORMATION FOR SEQ ID NO:14:

(i) SEQUENCE CHARACTERISTICS:
        (A) LENGTH: 80 amino acids
        (B) TYPE: amino acid
        (D) TOPOLOGY: linear (ii) MOLECULE TYPE: peptide (xi) SEQUENCE DESCRIPTION: SEQ ID NO:14:

Met Lys Ser Asn Asn Ala Leu Ile Val Ile Leu Gly Thr Val Thr Leu
    1               5                   10                  15

Asp Ala Val Gly Ile Gly Leu Val Met Pro Val Leu Pro Gly Leu Leu
                    20                  25                  30

Arg Asp Ile Arg Leu Met Arg Glu Arg Asp Gly Arg Asn His Arg Asp
                35                  40                  45

Met Cys Val Leu Phe Arg Trp Ala Cys Gln Asp Asn Phe Trp Ser Gly
        50                  55                  60

Asn Val Leu Ser Pro Ala Lys Leu Thr Pro His Pro Pro Val Asp Asn
    65                  70                  75                  80

(2) INFORMATION FOR SEQ ID NO:15:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:15:

Met Cys Gly Ile Val Ser Gly
    1               5

(2) INFORMATION FOR SEQ ID NO:16:

(i) SEQUENCE CHARACTERISTICS:
        (A) LENGTH: 237 amino acids
        (B) TYPE: amino acid
        (D) TOPOLOGY: linear (ii) MOLECULE TYPE: peptide (xi) SEQUENCE DESCRIPTION: SEQ ID NO:16:

```
Met His Met Lys Asn Ile Lys Lys Asn Gln Val Met Asn Leu Gly Pro
 1               5                  10                  15
Asn Ser Lys Leu Leu Lys Glu Tyr Lys Ser Gln Leu Ile Glu Leu Asn
                20                  25                  30
Ile Glu Gln Phe Glu Ala Gly Ile Gly Leu Ile Leu Gly Asp Ala Tyr
                35                  40                  45
Ile Arg Ser Arg Asp Glu Gly Lys Thr Tyr Cys Met Gln Phe Glu Trp
    50                  55                  60
Lys Asn Lys Ala Tyr Met Asp His Val Cys Leu Leu Tyr Asp Gln Trp
65                  70                  75                  80
Val Leu Ser Pro Pro His Lys Lys Glu Arg Val Asn His Leu Gly Asn
                85                  90                  95
Leu Val Ile Thr Trp Gly Ala Gln Thr Phe Lys His Gln Ala Phe Asn
                100                 105                 110
Lys Leu Ala Asn Leu Phe Ile Val Asn Asn Lys Lys Thr Ile Pro Asn
                115                 120                 125
Asn Leu Val Glu Asn Tyr Leu Thr Pro Met Ser Leu Ala Tyr Trp Phe
                130                 135                 140
Met Asp Asp Gly Gly Lys Trp Asp Tyr Asn Lys Asn Ser Thr Asn Lys
145                 150                 155                 160
Ser Ile Val Leu Asn Thr Gln Ser Phe Thr Phe Glu Glu Val Glu Tyr
                165                 170                 175
Leu Val Lys Gly Leu Arg Asn Lys Phe Gln Leu Asn Cys Tyr Val Lys
                180                 185                 190
Ile Asn Lys Asn Lys Pro Ile Ile Tyr Ile Asp Ser Met Ser Tyr Leu
                195                 200                 205
Ile Phe Tyr Asn Leu Ile Lys Pro Tyr Leu Ile Pro Gln Met Met Tyr
                210                 215                 220
Lys Leu Pro Asn Thr Ile Ser Ser Glu Thr Phe Leu Lys
225                 230                 235
```

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGCTAGGGAT AACAGGGTAA TATAGC                                       26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:18:

GCGATCCCTA TTGTCCCATT ATATCG                                26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TTCTCATGAT TAGCTCTAAT CCATGG                                26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AAGAGTACTA ATCGAGATTA GGTACC                                26

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CTTTGGTCAT CCAGAAGTAT ATATTT                                26

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GAAACCAGTA GGTCTTCATA TATAAA                                26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TAACGGTCCT AAGGTAGCGA AATTCA                                             26

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

ATTGCCAGGA TTCCATCGCT TTAAGT                                             26

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGACTCTCTT AAGGTAGCCA AATGCC                                             26

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

ACTGAGAGAA TTCCATCGGT TTACGG                                             26

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CGAGGTTTTG GTAACTATTT ATTACC                                             26

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CCTCCAAAAC CATTGATAAA TAATGG                                             26

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGGTTCAAAA CGTCGTGAGA CAGTTT                                                  26

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CCCAAGTTTT GCAGCACTCT GTCAAA                                                  26

(2) INFORMATION FOR SEQ ID NO:31:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GATGCTGTAG GCATAGGCTT GGTTAT                                                  26

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CTACGACATC CGTATCCGAA CCAATA                                                  26

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CTTTCCGCAA CAGTATAATT TTATAA                                                  26

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:34:

GAAAGGCGTT GTCATATTAA AATATT                                              26

(2) INFORMATION FOR SEQ ID NO:35:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

ACCATGGGGT CAAATGTCTT TCTGGG                                              26

(2) INFORMATION FOR SEQ ID NO:36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

TGGTACCCCA GTTTACAGAA AGACCC                                              26

(2) INFORMATION FOR SEQ ID NO:37:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

GTGCCTGAAT GATATTTATT ACCTTT                                              26

(2) INFORMATION FOR SEQ ID NO:38:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

GTGCCTGAAT GATATTTATT ACCTTT                                              26

(2) INFORMATION FOR SEQ ID NO:39:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

```
CAACGCTCAG TAGATGTTTT CTTGGGTCTA CCGTTTAAT                                39
```

(2) INFORMATION FOR SEQ ID NO:40:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
GTTGCGAGTC ATCTACAAAA GAACCCAGAT GGCAAATTA                                39
```

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
CAAGCTTATG AGTATGAAGT GAACACGTTA TT                                       32
```

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
GTTCGAATAC TCATACTTCA CTTGTGCAAT AA                                       32
```

(2) INFORMATION FOR SEQ ID NO:43:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
GCTATTCGTT TTTATGTATC TTTTGCGTGT AGCTTTAA                                 38
```

(2) INFORMATION FOR SEQ ID NO:44:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
CGATAAGCAA AAATACATAG AAAACGCACA TGGAAATT                                 38
```

(2) INFORMATION FOR SEQ ID NO:45:

(i) SEQUENCE CHARACTERISTICS:
    (A) LENGTH: 80 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:45:

```
CCAAGCTCGA ATTCGCATGC TCTAGAGCTC GGTACCCGGG ATCCTGCAGT CGACGCTAGG      60

GATAACAGGG TAATACAGAT                                                 80
```

(2) INFORMATION FOR SEQ ID NO:46:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
GGTTCGAGCT TAAGCGTACG AGATCTCGAG CCATGGGCCC TAGGACGTCA GCTGCGATCC      60

CTATTGTCCC ATTATGTCTA                                                 80
```

(2) INFORMATION FOR SEQ ID NO:47:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

```
ATCAGATCTA AGCTTGCATG CCTGCAGGTC GACTCTAGAG GATCCCCGGG TACCGAGCTC      60

GAATTCACTG GCCGTCGTTT                                                 80
```

(2) INFORMATION FOR SEQ ID NO:48:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

```
TAGTCTAGAT TCGAACGTAC GGACGTCCAG CTGAGATCTC CTAGGGGCCC ATGGCTCGAG      60

CTTAAGTGAC CGGCAGCAAA                                                 80
```

(2) INFORMATION FOR SEQ ID NO:49:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
TACAACGTCG TGACTGGGAA AACCCTGGCG TTACCCAACT TAATCGCCTT GCAGCACATC      60
```

CCCCTTTCGC CAGCTGGCGT                                                   80

(2) INFORMATION FOR SEQ ID NO:50:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

ATGTTGCAGC ACTGACCCTT TTGGGACCGC AATGGGTTGA ATTAGCGGAA CGTCGTGTAG    60

GGGGAAAGCG GTCGACCGCA                                                80

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

TAGGGATAAC AGGGTAAT                                                  18

(2) INFORMATION FOR SEQ ID NO:52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

ATCCCTATTG TCCCATTA                                                  18

NUCLEOTIDE SEQUENCE ENCODING THE ENZYME I-SCEI AND THE USES THEREOF

CROSS-REFERENCE TO RELATED APPLICATION

This is a division of application Ser. No. 07/971,160, filed Nov. 5, 1992, now U.S. Pat. No. 5,474,896, which is a continuation-in-part application of Ser. No. 07/879,689, filed May 5, 1992 now abandoned. The entire disclosure of the prior application is relied upon and incorporated herein by reference.

BACKGROUND OF THE INVENTION

This invention relates to a nucleotide sequence that encodes the restriction endonuclease I-SceI. This invention also relates to vectors containing the nucleotide sequence, cells transformed with the vectors, transgenic animals based on the vectors, and cell lines derived from cells in the animals. This invention also relates to the use of I-SceI for mapping eukaryotic genomes and for in vivo site directed genetic recombination.

The ability to introduce genes into the germ line of mammals is of great interest in biology. The propensity of mammalian cells to take up exogenously added DNA and to express genes included in the DNA has been known for many years. The results of gene manipulation are inherited by the offspring of these animals. All cells of these offspring inherit the introduced gene as part of their genetic make-up. Such animals are said to be transgenic.

Transgenic mammals have provided a means for studying gene regulation during embryogenesis and in differentiation, for studying the action of genes, and for studying the intricate interaction of cells in the immune system. The whole animal is the ultimate assay system for manipulated genes, which direct complex biological processes.

Transgenic animals can provide a general assay for functionally dissecting DNA sequences responsible for tissue specific or developmental regulation of a variety of genes. In addition, transgenic animals provide useful vehicles for expressing recombinant proteins and for generating precise animal models of human genetic disorders.

For a general discussion of gene cloning and expression in animals and animal cells, see Old and Primrose, "Principles of Gene Manipulation," Blackwell Scientific Publications, London (1989), page 255 et seq.

Transgenic lines, which have a predisposition to specific diseases and genetic disorders, are of great value in the investigation of the events leading to these states. It is well known that the efficacy of treatment of a genetic disorder may be dependent on identification of the gene defect that is the primary cause of the disorder. The discovery of effective treatments can be expedited by providing an animal model that will lead to the disease or disorder, which will enable the study of the efficacy, safety, and mode of action of treatment protocols, such as genetic recombination.

One of the key issues in understanding genetic recombination is the nature of the initiation step. Studies of homologous recombination in bacteria and fungi have led to the proposal of two types of initiation mechanisms. In the first model, a single-strand nick initiates strand assimilation and branch migration (Meselson and Radding 1975). Alternatively, a double-strand break may occur, followed by a repair mechanism that uses an uncleaved homologous sequence as a template (Resnick and Martin 1976). This latter model has gained support from the fact that integrative transformation in yeast is dramatically increased when the transforming plasmid is linearized in the region of chromosomal homology (Orr-Weaver, Szostak and Rothstein 1981) and from the direct observation of a double-strand break during mating type interconversion of yeast (Strathern et al. 1982). Recently, double-strand breaks have also been characterized during normal yeast meiotic recombination (Sun et al. 1989; Alani, Padmore and Kleckner 1990).

Several double-strand endonuclease activities have been characterized in yeast: HO and intron encoded endonucleases are associated with homologous recombination functions, while others still have unknown genetic functions (Endo-SceI, Endo-SceII) (Shibata et al. 1984; Morishima et al. 1990). The HO site-specific endonuclease initiates mating-type interconversion by making a double-strand break near the YZ junction of MAT (Kostriken et al. 1983). The break is subsequently repaired using the intact HML or HMR sequences and resulting in ectopic gene conversion. The HO recognition site is a degenerate 24 bp non-symmetrical sequence (Nickoloff, Chen, and Heffron 1986; Nickoloff, Singer and Heffron 1990). This sequence has been used as a "recombinator" in artificial constructs to promote intra- and intermolecular mitotic and meiotic recombination (Nickoloff, Chen and Heffron, 1986; Kolodkin, Klar and Stahl 1986; Ray et al. 1988, Rudin and Haber, 1988; Rudin, Sugarman, and Haber 1989).

The two-site specific endonucleases, I-SceI (Jacquier and Dujon 1985) and I-SceII (Delahodde et al. 1989; Wenzlau et al. 1989), that are responsible for intron mobility in mitochondria, initiate a gene conversion that resembles the HO-induced conversion (see Dujon 1989 for review). I-SceI, which is encoded by the optional intron Sc LSU.1 of the 21S rRNA gene, initiates a double-strand break at the intron insertion site (Macreadie et al. 1985; Dujon et al. 1985; Colleaux et al. 1986). The recognition site of I-SceI extends over an 18 bp non-symmetrical sequence (Colleaux et al. 1988). Although the two proteins are not obviously related by their structure (HO is 586 amino acids long while I-SceI is 235 amino acids long), they both generate 4 bp staggered cuts with 3'OH overhangs within their respective recognition sites. It has been found that a mitochondrial intron-encoded endonuclease, transcribed in the nucleus and translated in the cytoplasm, generates a double-strand break at a nuclear site. The repair events induced by I-SceI are identical to those initiated by HO.

In summary, there exists a need in the art for reagents and methods for providing transgenic animal models of human diseases and genetic disorders. The reagents can be based on the restriction enzyme I-SceI and the gene encoding this enzyme. In particular, there exists a need for reagents and methods for replacing a natural gene with another gene that is capable of alleviating the disease or genetic disorder.

SUMMARY OF THE INVENTION

Accordingly, this invention aids in fulfilling these needs in the art. Specifically, this invention relates to an isolated DNA encoding the enzyme I-SceI. The DNA has the following nucleotide sequence:

```
                          (SEQ ID NO:1)  ATG CAT
                                          M   H

ATG AAA AAC ATC AAA AAA AAC CAG GTA ATG  2670
      M   K   N   I   K   K   N   Q   V   M    12

2671 AAC CTC GGT CCG AAC TCT AAA CTG CTG AAA
```

```
 13 N   L   G   P   N   S   K   L   L   K

GAA TAC AAA TCC CAG CTG ATC GAA CTG AAC 2730
     E   Y   K   S   Q   L   I   E   L   N   32

2731 ATC GAA CAG TTC GAA GCA GGT ATC GGT CTG
  33 I   E   Q   F   E   A   G   I   G   L

ATC CTG GGT GAT GCT TAC ATC CGT TCT CGT 2790
     I   L   G   D   A   Y   I   R   S   R   52

2791 GAT GAA GGT AAA ACC TAC TGT ATG CAG TTC
  53 D   E   G   K   T   Y   C   M   Q   F

GAG TGG AAA AAC AAA GCA TAC ATG GAC CAC 2850
     E   W   K   N   K   A   Y   M   D   H   72

2851 GTA TGT CTG CTG TAC GAT CAG TGG GTA CTG
  73 V   C   L   L   Y   D   Q   W   V   L

TCC CCG CCG CAC AAA AAA GAA CGT GTT AAC 2910
     S   P   P   H   K   K   E   R   V   N   92

2911 CAC CTG GGT AAC CTG GTA ATC ACC TGG GGC
  93 H   L   G   N   L   V   I   T   W   G

GCC CAG ACT TTC AAA CAC CAA GCT TTC AAC 2970
     A   Q   T   F   K   H   Q   A   F   N   112

2971 AAA CTG GCT AAC CTG TTC ATC GTT AAC AAC
 113 K   L   A   N   L   F   I   V   N   N

AAA AAA ACC ATC CCG AAC AAC CTG GTT GAA 3030
     K   K   T   I   P   N   N   L   V   E   132

3031 AAC TAC CTG ACC CCG ATG TCT CTG GCA TAC
 133 N   Y   L   T   P   M   S   L   A   Y

TGG TTC ATG GAT GAT GGT GGT AAA TGG GAT 3090
     W   F   M   D   D   G   G   K   W   D   152

3091 TAC AAC AAA AAC TCT ACC AAC AAA TCG ATC
 153 Y   N   K   N   S   T   N   K   S   I

GTA CTG AAC ACC CAG TCT TTC ACT TTC GAA 3150
     V   L   N   T   Q   S   F   T   F   E   172

3151 GAA GTA GAA TAC CTG GTT AAG GGT CTG CGT
 173 E   V   E   Y   L   V   K   G   L   R

AAC AAA TTC CAA CTG AAC TGT TAC GTA AAA 3210
     N   K   F   Q   L   N   C   Y   V   K   192

3211 ATC AAC AAA AAC AAA CCG ATC ATC TAC ATC
 193 I   N   K   N   K   P   I   I   Y   I

GAT TCT ATG TCT TAC CTG ATC TTC TAC AAC 3270
     D   S   M   S   Y   L   I   F   Y   N   212

3271 CTG ATC AAA CCG TAC CTG ATC CCG CAG ATG
 213 L   I   K   P   Y   L   I   P   Q   M

ATG TAC AAA CTG CCG AAC ACT ATC TCC TCC 3330
     M   Y   K   L   P   N   T   I   S   S   232

3331 GAA ACT TTC CTG AAA TAA
 233 E   T   F   L   K   *
```

This invention also relates to a DNA sequence comprising a promoter operatively linked to the DNA sequence of the invention encoding the enzyme I-SceI.

This invention further relates to an isolated RNA complementary to the DNA sequence of the invention encoding the enzyme I-SceI and to the other DNA sequences described herein.

In another embodiment of the invention, a vector is provided. The vector comprises a plasmid, bacteriophage, or cosmid vector containing the DNA sequence of the invention encoding the enzyme I-SceI.

In addition, this invention relates to E. coli or eukaryotic cells transformed with a vector of the invention.

Also, this invention relates to transgenic animals containing the DNA sequence encoding the enzyme I-SceI and cell lines cultured from cells of the transgenic animals.

In addition, this invention relates to a transgenic organism in which at least one restriction site for the enzyme I-SceI has been inserted in a chromosome of the organism.

Further, this invention relates to a method of genetically mapping a eukaryotic genome using the enzyme I-SceI.

This invention also relates to a method for in vivo site directed recombination in an organism using the enzyme I-SceI.

BRIEF DESCRIPTION OF THE DRAWINGS

This invention will be more fully described with reference to the drawings in which:

FIG. 1 depicts the universal code equivalent of the mitochondrial I-SceI gene (SEQ ID NOS:3 and 4).

FIG. 2 depicts the nucleotide sequence of the invention encoding the enzyme I-SceI and the amino acid sequence of the natural I-SceI enzyme (SEQ ID NOS:5 and 2).

FIGS. 4A and 4B are the nucleotide sequence and deduced amino acid sequence of a region of plasmid pSCM525. The nucleotide sequence of the invention encoding the enzyme I-SceI is enclosed in the box (SEQ ID NOS:9 through 16). Note the two amino acid N-terminal extension as compared to the genuine version of the gene.

FIG. 5 depicts variations around the amino acid sequence of the enzyme I-SceI (SEQ ID NO:2).

FIG. 6 shows Group I intron encoding endonucleases and related endonucleases (SEQ ID NOS:17 through 44).

FIGS. 10A and 10B show the nucleotide sequence and restriction sites of regions of the plasmid PAF100 (SEQ ID NOS:45 through 50).

FIGS. 13A, 13B, and 13C depict an insertion vector PMLV LTR SAPLZ containing the I-SceI site for mammalian cells.

FIGS. 16A, 16B, and 16C depict mapping of the I-SceI sites of transgenic yeast strains by hybridization with left end and right end probes of chromosome XI. Chromosomes from FY1679 (control) and the seven transgenic yeast strains were digested with I-SceI. Transgenic strains were placed in order as explained in FIG. 15. Electrophoresis conditions were as in FIG. 14. $^{32}$P labelled cosmids pUKG040 and pUKG066 were used as left end and right end probes, respectively.

DETAILED DESCRIPTION OF THE PREFERRED EMBODIMENTS

Figure 3:
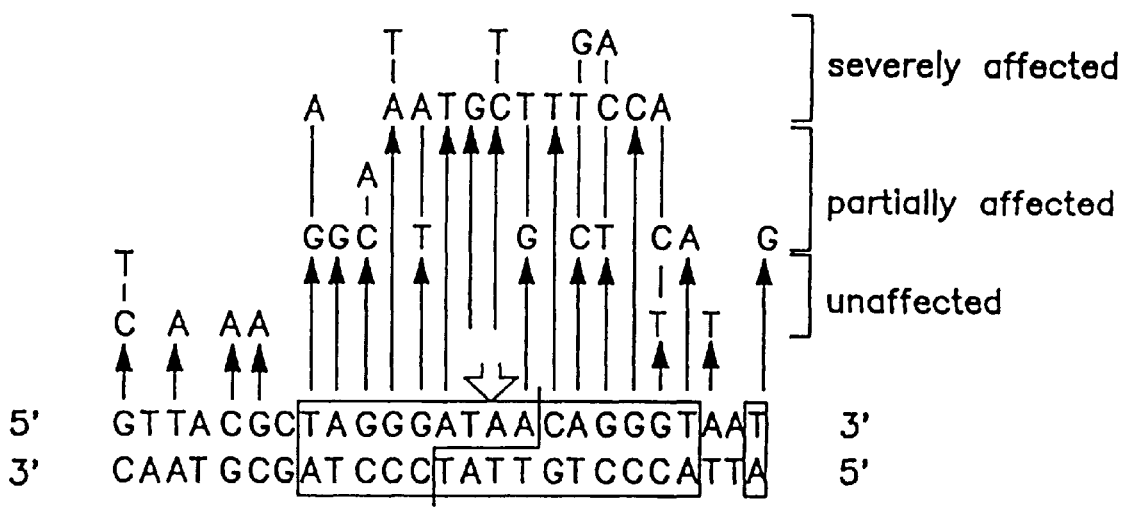
FIG. 3 depicts the I-SceI recognition sequence and indicates possible base mutations in the recognition site and the effect of such mutations on stringency of recognition (SEQ ID NOS:5, 6, 7 and 8).

The genuine mitochondrial gene (ref. 8) cannot be expressed in *E. coli*, yeast or other organisms due to the peculiarities of the mitochondrial genetic code. A "universal code equivalent" has been constructed by in vitro site-directed mutagenesis. Its sequence is given in FIG. 1. Note that all non-universal codons (except two CTN) have been replaced together with some codons extremely rare in *E. coli*.

The universal code equivalent has been successfully expressed in *E. coli* and determines the synthesis of an active enzyme. However, expression levels remained low due to the large number of codons that are extremely rare in *E. coli*. Expression of the "universal code equivalent" has been detected in yeast.

To optimize gene expression in heterologous systems, a synthetic gene has been designed to encode a protein with the genuine amino acid sequence of I-SceI using, for each codon, that most frequently used in *E. coli*. The sequence of the synthetic gene is given in FIG. 2. The synthetic gene was constructed in vitro from eight synthetic oligonucleotides with partial overlaps. Oligonucleotides were designed to allow mutual priming for second strand synthesis by Klenow polymerase when annealed by pairs. The elongated pairs were then ligated into plasmids. Appropriately placed restriction sites within the designed sequence allowed final assembly of the synthetic gene by in vitro ligation. The synthetic gene has been successfully expressed in both *E. coli* and yeast.

1. I-SceI Gene Sequence

This invention relates to an isolated DNA sequence encoding the enzyme I-SceI. The enzyme I-SceI is an endonuclease. The properties of the enzyme (ref. 14) are as follows:

I-SceI is a double-stranded endonuclease that cleaves DNA within its recognition site. I-SceI generates a 4 bp staggered cut with 3'OH overhangs.

Substrate: Acts only on double-stranded DNA. Substrate DNA can be relaxed or negatively supercoiled.

Cations: Enzymatic activity requires $Mg^{++}$ (8 mM is optimum). $Mn^{++}$ can replace $Mg^{++}$, but this reduces the stringency of recognition.

Optimum conditions for activity: high pH (9 to 10), temperature 20–40° C., no monovalent cations.

Enzyme stability: I-SceI is unstable at room temperature. The enzyme-substrate complex is more stable than the enzyme alone (presence of recognition sites stabilizes the enzyme.)

The enzyme I-SceI has a known recognition site. (ref. 14.) The recognition site of I-SceI is a non-symmetrical sequence that extends over 18 bp as determined by systematic mutational analysis. The sequence reads: (arrows indicate cuts).

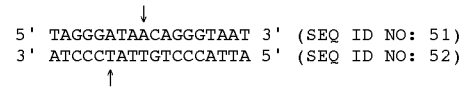

The recognition site corresponds, in part, to the upstream exon and, in part, to the downstream exon of the intron plus form of the gene.

The recognition site is partially degenerate: single base substitutions within the 18 bp long sequence result in either complete insensitivity or reduced sensitivity to the enzyme, depending upon position and nature of the substitution.

The stringency of recognition has been measured on:

1 mutants of the site.

2 the total yeast genome (*Saccharomyces cerevisiae*, genome complexity is 1.4×10 bp). Data are unpublished.

Results are

1 Mutants of the site: As shown in FIG. 3, there is a general shifting of stringency, i.e., mutants severely affected in Mg++ become partially affected in Mn++, mutants partially affected in Mg++ become unaffected in Mn++.

2 Yeast: In magnesium conditions, no cleavage is observed in normal yeast. In the same condition, DNA from transgenic yeasts is cleaved to completion at the artificially inserted I-SceI site and no other cleavage site can be detected. If magnesium is replaced by manganese, five additional cleavage sites are revealed in the entire yeast genome, none of which is cleaved to completion. Therefore, in manganese the enzyme reveals an average of 1 site for ca. 3 millions based pairs ($5/1.4\times10^7$ bp).

Definition of the Recognition Site

Important bases are indicated in FIG. 3. They correspond to bases for which severely affected mutants exist. Notice however that:

1 All possible mutations at each position have not been determined; therefore a base that does not correspond to a severely affected mutant may still be important if another mutant was examined at this very same position.

2 There is no clear-cut limit between a very important base (all mutants are severely affected) and a moderately important base (some of the mutants are severely affected). There is a continuum between excellent substrates and poor substrates for the enzyme.

The expected frequency of natural I-SceI sites in a random DNA sequence is, therefore, equal to $(0.25)^{-18}$ or $(1.5\times10^{-11})$. In other words, one should expect one natural site for the equivalent of ca. 20 human genomes, but the frequency of degenerate sites is more difficult to predict.

I-SceI belongs to a "degenerate" subfamily of the two-dodecapeptide family. Conserved amino acids of the dodecapeptide motifs are required for activity. In particular, the aspartic residues at positions 9 of the two dodecapeptides cannot be replaced, even with glutamic residues. It is likely that the dodecapeptides form the catalytic site or part of it.

Consistent with the recognition site being non-symmetrical, it is likely that the endonucleolytic activity of I-SceI requires two successive recognition steps: binding of the enzyme to the downstream half of the site (corresponding to the downstream exon) followed by binding of the enzyme to the upstream half of the site (corresponding to the upstream exon). The first binding is strong, the second is weaker, but the two are necessary for cleavage of DNA. In vitro, the enzyme can bind the downstream exon alone as well as the intronexon junction sequence, but no cleavage results.

The evolutionarily conserved dodecapeptide motifs of intron-encoded I-SceI are essential for endonuclease activity. It has been proposed that the role of these motifs is to properly position the acidic amino acids with respect to the DNA sequence recognition domains of the enzyme for the catalysis of phosphodiester bond hydrolysis (ref. P3).

The nucleotide sequence of the invention, which encodes the natural I-SceI enzyme is shown in FIG. 2. The nucleotide sequence of the gene of the invention was derived by dideoxynucleotide sequencing. The base sequences of the nucleotides are written in the 5'→3' direction. Each of the letters shown is a conventional designation for the following nucleotides:

A Adenine
G Guanine
T Thymine
C Cytosine.

It is preferred that the DNA sequence encoding the enzyme I-SceI be in a purified form. For instance, the sequence can be free of human blood-derived proteins, human serum proteins, viral proteins, nucleotide sequences encoding these proteins, human tissue, human tissue components, or combinations of these substances. In addition, it is preferred that the DNA sequence of the invention is free of extraneous proteins and lipids, and adventitious microorganisms, such as bacteria and viruses. The essentially purified and isolated DNA sequence encoding I-SceI is especially useful for preparing expression vectors.

Figure 4B:
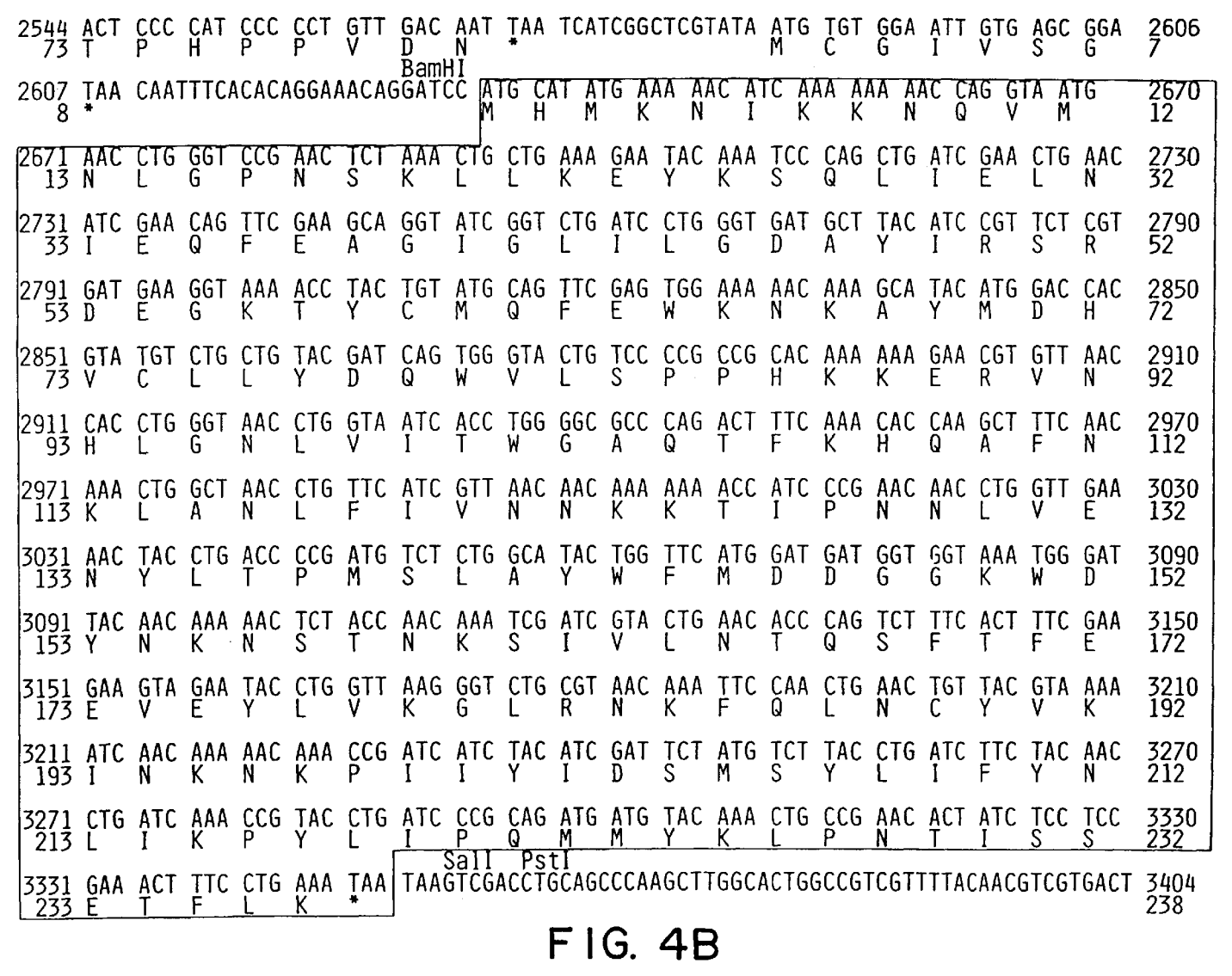

Plasmid pSCM525 is a pUC12 derivative, containing an artificial sequence encoding the DNA sequence of the invention. The nucleotide sequence and deduced amino acid sequence of a region of plasmid pSCM525 is shown in FIG. 4. The nucleotide sequence of the invention encoding I-SceI is enclosed in the box. The artificial gene is a BamHI-SalI piece of DNA sequence of 723 base pairs, chemically synthesized and assembled. It is placed under tac promoter control. The DNA sequence of the artificial gene differs from the natural coding sequence or its universal code equivalent described in Cell (1986), Vol. 44, pages 521–533. However, the translation product of the artificial gene is identical in sequence to the genuine omega-endonuclease except for the addition of a Met-His at the N-terminus. It will be understood that this modified endonuclease is within the scope of this invention.

Plasmid pSCM525 can be used to transform any suitable E. coli strain and transformed cells become ampicillin-resistant. Synthesis of the omega-endonuclease is obtained by addition of I.P.T.G. or an equivalent inducer of the lactose operon system.

A plasmid identified as pSCM525 containing the enzyme I-SceI was deposited in E. coli strain TG1 with the Collection Nationale de Cultures de Microorganismes (C.N.C.M.) of Institut Pasteur in Paris, France on Nov. 22, 1990, under culture collection deposit Accession No. 1-1014. The nucleotide sequence of the invention is thus available from this deposit.

The gene of the invention can also be prepared by the formation of 3'→5' phosphate linkages between nucleoside units using conventional chemical synthesis techniques. For example, the well-known phosphodiester, phosphotriester, and phosphite triester techniques, as well as known modifications of these approaches, can be employed. Deoxyribonucleotides can be prepared with automatic synthesis machines, such as those based on the phosphoramidite approach. Oligo- and polyribonucleotides can also be obtained with the aid of RNA ligase using conventional techniques.

This invention of course includes variants of the DNA sequence of the invention exhibiting substantially the same properties as the sequence of the invention. By this it is meant that DNA sequences need not be identical to the sequence disclosed herein. Variations can be attributable to single or multiple base substitutions, deletions, or insertions or local mutations involving one or more nucleotides not substantially detracting from the properties of the DNA sequence as encoding an enzyme having the cleavage properties of the enzyme I-SceI.

FIG. 5 depicts some of the variations that can be made around the I-SceI amino acid sequence. It has been demonstrated that the following positions can be changed without affecting enzyme activity:

positions −1 and −2 are not natural. The two amino acids are added due to cloning strategies.

positions 1 to 10: can be deleted.

position 36: G is tolerated.

position 40: M or V are tolerated.

position 41: S or N are tolerated.

position 43: A is tolerated.

position 46: V or N are tolerated.

position 91: A is tolerated.

positions 123 and 156: L is tolerated.

position 223: A and S are tolerated.

It will be understood that enzymes containing these modifications are within the scope of this invention.

Changes to the amino acid sequence in FIG. 5 that have been demonstrated to affect enzyme activity are as follows:

position 19: L to S position 38: I to S or N position 39: G to D or R position 40: L to Q position 42: L to R position 44: D to E, G or H position 45: A to E or D position 46: Y to D position 47: I to R or N position 80: L to S position 144: D to E position 145: D to E position 146: G to E position 147: G to S It will also be understood that the present invention is intended to encompass fragments of the DNA sequence of the invention in purified form, where the fragments are capable of encoding enzymatically active I-SceI.

The DNA sequence of the invention coding for the enzyme I-SceI can be amplified in the well known polymerase chain reaction (PCR), which is useful for amplifying all or specific regions of the gene. See e.g., S. Kwok et al., J. Virol., 61:1690–1694 (1987); U.S. Pat. No. 4,683,202; and U.S. Pat. No. 4,683,195. More particularly, DNA primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the DNA. The PCR reaction mixture can contain the DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the DNA at an elevated temperature, cooling of the reaction mixture, and polymerization with the DNA polymerase. Amplified sequences can be detected by the use of a technique termed oligomer restriction (OR). See, R. K. Saiki et al., Bio/Technology 3:1008–1012 (1985).

The enzyme I-SceI is one of a number of endonucleases with similar properties. Following is a listing of related enzymes and their sources.

Group I intron encoded endonucleases and related enzymes are listed below with references. Recognition sites are shown in FIG. 6.

| Enzyme | Encoded by | Ref |
|---|---|---|
| I-SceI | Sc LSU-1 intron | this work |
| I-SceII | Sc cox1-4 intron | Sargueil et al., NAR (1990) 18, 5659–5665 |
| I-SceIII | Sc cox1-3 intron | Sargueil et al., MGG (1991) 225, 340–341 |
| I-SceIV | Sc cox1-5a intron | Seraphin et al. (1992) in press |
| I-CeuI | Ce LSU-5 intron | Marshall, Lemieux Gene (1991) 104, 241–245 |
| I-CreI | Cr LSU-1 intron | Rochaix (unpublished) |
| I-PpoI | Pp LSU-3 intron | Muscarella et al., MCB (1990) 10, 3386–3396 |
| I-TevI | T4 td-1 intron | Chu et al., PNAS (1990) 87, 3574–3578 and Bell-Pedersen et al. NAR (1990) 18, 3763–3770. |
| I-TevII | T4 sunY intron | Bell-Pedersen et al. NAR (1990) 18, 3763–3770. |
| I-TevIII | RB3 nrdB-1 intron | Eddy, Gold, Genes Dev. (1991) 5, 1032–1041 |
| HO | HO yeast gene | Nickoloff et al., MCB (1990) 10, 1174–1179 |
| Endo SceI | RF3 yeast mito. gene | Kawasaki et al., JBC (1991) 266, 5342–5347 |

Putative new enzymes (genetic evidence but no activity as yet) are I-CsmI from cytochrome b intron 1 of *Chlamydomonas smithii* mitochondria (ref. 15), I-PanI from cytochrome b intron 3 of *Podospora anserina* mitochondria (Jill Salvo), and probably enzymes encoded by introns Nc nd1•1 and Nc cob•! from *Neurospora crassa*.

The I-endonucleases can be classified as follows:

Class I: Two dodecapeptide motifs, 4 bp staggered cut with 3' OH overhangs, cut internal to recognition site

| Subclass "I-SceI" | Other subclasses |
|---|---|
| I-SceI | I-SceII |
| I-SceIV | I-SceIII |
| I-CsmI | I-CeuI (only one dodecapeptide motif) |
| I-PanI | I-CreI (only one dodecapeptide motif) |
| | HO |
| | TFP1-408 (HO homolog) |
| | Endo SceI |

Class II: GIY-($N_{10-11}$) YIG motif, 2 bp staggered cut with 3' OH overhangs, cut external to recognition site:
  I-TevI Class III: no typical structural motifs, 4 bp staggered cut with 3' OH overhangs, cut internal to recognition site:
  I-PpoI Class IV: no typical structural motifs, 2 bp staggered cut with 3' OH overhangs, cut external to recognition site:
  I-TevII Class V: no typical structural motifs, 2 bp staggered cut with 5' OH overhangs:
  I-TevIII.

2. Nucleotide Probes Containing the I-SceI Gene of the Invention

The DNA sequence of the invention coding for the enzyme I-SceI can also be used as a probe for the detection of a nucleotide sequence in a biological material, such as tissue or body fluids. The probe can be labeled with an atom or inorganic radical, most commonly using a radionuclide, but also perhaps with a heavy metal. Radioactive labels include $^{32}P$, $^{3}H$, $^{14}C$, or the like. Any radioactive label can be employed, which provides for an adequate signal and has sufficient half-life. Other labels include ligands that can serve as a specific binding member to a labeled antibody, fluorescers, chemiluminescers, enzymes, antibodies which can serve as a specific binding pair member for a labeled ligand, and the like. The choice of the label will be governed by the effect of the label on the rate of hybridization and binding of the probe to the DNA or RNA. It will be necessary that the label provide sufficient sensitivity to detect the amount of DNA or RNA available for hybridization.

When the nucleotide sequence of the invention is used as a probe for hybridizing to a gene, the nucleotide sequence is preferably affixed to a water insoluble solid, porous support, such as nitrocellulose paper. Hybridization can be carried out using labeled polynucleotides of the invention and conventional hybridization reagents. The particular hybridization technique is not essential to the invention.

The amount of labeled probe present in the hybridization solution will vary widely, depending upon the nature of the label, the amount of the labeled probe which can reasonably bind to the support, and the stringency of the hybridization. Generally, substantial excesses of the probe over stoichiometric will be employed to enhance the rate of binding of the probe to the fixed DNA.

Various degrees of stringency of hybridization can be employed. The more severe the conditions, the greater the complementarity that is required for hybridization between the probe and the polynucleotide for duplex formation. Severity can be controlled by temperature, probe concentration, probe length, ionic strength, time, and the like. Conveniently, the stringency of hybridization is varied by changing the polarity of the reactant solution. Temperatures to be employed can be empirically determined or determined from well known formulas developed for this purpose.

3. Nucleotide Sequences Containing the Nucleotide Sequence Encoding I-SceI

This invention also relates to the DNA sequence of the invention encoding the enzyme I-SceI, wherein the nucleotide sequence is linked to other nucleic acids. The nucleic acid can be obtained from any source, for example, from plasmids, from cloned DNA or RNA, or from natural DNA or RNA from any source, including prokaryotic and eukaryotic organisms. DNA or RNA can be extracted from a biological material, such as biological fluids or tissue, by a variety of techniques including those described by Maniatis et al., *Molecular Cloning: A Laboratory Manual,* Cold Spring Harbor Laboratory, New York (1982). The nucleic acid will generally be obtained from a bacteria, yeast, virus, or a higher organism, such as a plant-or animal. The nucleic acid can be a fraction of a more complex mixture, such as a portion of a gene contained in whole human DNA or a portion of a nucleic acid sequence of a particular microorganism. The nucleic acid can be a fraction of a larger molecule or the nucleic acid can constitute an entire gene or assembly of genes. The DNA can be in a single-stranded or double-stranded form. If the fragment is in single-stranded form, it can be converted to double-stranded form using DNA polymerase according to conventional techniques.

The DNA sequence of the invention can be linked to a structural gene. As used herein, the term "structural gene" refers to a DNA sequence that encodes through its template or messenger MRNA a sequence of amino acids characteristic of a specific protein or polypeptide. The nucleotide sequence of the invention can function with an expression control sequence, that is, a DNA sequence that controls and regulates expression of the gene when operatively linked to the gene.

4. Vectors Containing the Nucleotide Sequence of the Invention

This invention also relates to cloning and expression vectors containing the DNA sequence of the invention coding for the enzyme I- SceI.

More particularly, the DNA sequence encoding the enzyme can be ligated to a vehicle for cloning the sequence. The major steps involved in gene cloning comprise procedures for separating DNA containing the gene of interest from prokaryotes or eukaryotes, cutting the resulting DNA fragment and the DNA from a cloning vehicle at specific sites, mixing the two DNA fragments together, and ligating the fragments to yield a recombinant DNA molecule. The recombinant molecule can then be transferred into a host cell, and the cells allowed to replicate to produce identical cells containing clones of the original DNA sequence.

The vehicle employed in this invention can be any double-stranded DNA molecule capable of transporting the nucleotide sequence of the invention into a host cell and capable of replicating within the cell. More particularly, the vehicle must contain at least one DNA sequence that can act as the origin of replication in the host cell. In addition, the vehicle must contain two or more sites for insertion of the DNA sequence encoding the gene of the invention. These sites will ordinarily correspond to restriction enzyme sites at which cohesive ends can be formed, and which are complementary to the cohesive ends on the promoter sequence to be ligated to the vehicle. In general, this invention can be carried out with plasmid, bacteriophage, or cosmid vehicles having these characteristics. For example, the vector SV-40 (Palmiter et al., Nature, 316:457–460 (1985)) or the plasmid pSVOAL, which is pSVOA, as described in EP 496174 A1, published Jul. 29, 1992, containing the luciferase gene (luc), may be the vehicle used to carry the nucleotide sequence of the claimed invention.

The nucleotide sequence of the invention can have cohesive ends compatible with any combination of sites in the vehicle. Alternatively, the sequence can have one or more blunt ends that can be ligated to corresponding blunt ends in the cloning sites of the vehicle. The nucleotide sequence to be ligated can be further processed, if desired, by successive exonuclease deletion, such as with the enzyme Bal 31. In the event that the nucleotide sequence of the invention does not contain a desired combination of cohesive ends, the sequence can be modified by adding a linker, an adaptor, or homopolymer tailing.

It is preferred that plasmids used for cloning nucleotide sequences of the invention carry one or more genes responsible for a useful characteristic, such as a selectable marker, displayed by the host cell. In a preferred strategy, plasmids having genes for resistance to two different drugs are chosen. For example, insertion of the DNA sequence into a gene for an antibiotic inactivates the gene and destroys drug resistance. The second drug resistance gene is not affected when cells are transformed with the recombinants, and colonies containing the gene of interest can be selected by resistance to the second drug and susceptibility to the first drug. Preferred antibiotic markers are genes imparting chloramphenicol, ampicillin, or tetracycline resistance to the host cell.

A variety of restriction enzymes can be used to cut the vehicle. The identity of the restriction enzyme will generally depend upon the identity of the ends on the DNA sequence to be ligated and the restriction sites in the vehicle. The restriction enzyme is matched to the restriction sites in the vehicle, which in turn is matched to the ends on the nucleic acid fragment being ligated.

The ligation reaction can be set up using well known techniques and conventional reagents. Ligation is carried out with a DNA ligase that catalyzes the formation of phosphodiester bonds between adjacent 5'-phosphate and the free 3'-hydroxy groups in DNA duplexes. The DNA ligase can be derived from a variety of microorganisms. The preferred DNA ligases are enzymes from *E. coli* and bacteriophage T4. T4 DNA ligase can ligate DNA fragments with blunt or sticky ends, such as those generated by restriction enzyme digestion. *E. coli* DNA ligase can be used to catalyze the formation of phosphodiester bonds between the termini of duplex DNA molecules containing cohesive ends.

Cloning can be carried out in prokaryotic or eukaryotic cells. The host for replicating the cloning vehicle will of course be one that is compatible with the vehicle and in which the vehicle can replicate. When a plasmid is employed, the plasmid can be derived from bacteria or some other organism or the plasmid can be synthetically prepared. The plasmid can replicate independently of the host cell chromosome or an integrative plasmid (episome) can be employed. The plasmid can make use of the DNA replicative enzymes of the host cell in order to replicate or the plasmid can carry genes that code for the enzymes required for plasmid replication. A number of different plasmids can be employed in practicing this invention.

The DNA sequence of the invention encoding the enzyme I-SceI can also be ligated to a vehicle to form an expression vector. The vehicle employed in this case is one in which it is possible to express the gene operatively linked to a promoter in an appropriate host cell. It is preferable to employ a vehicle known for use in expressing genes in *E. coli*, yeast, or mammalian cells. These vehicles include, for example, the following *E. coli* expression vectors:

pSCM525, which is an *E. coli* expression vector derived from pUC12 by insertion of a tac promoter and the synthetic gene for I-SceI. Expression is induced by IPTG.

pGEXω6, which is an *E. coli* expression vector derived from PGEX in which the synthetic gene from pSCM525 for I-SceI is fused with the glutathione S transferase gene, producing a hybrid protein. The hybrid protein possesses the endonuclease activity.

pDIC73, which is an *E. coli* expression vector derived from pET-3C by insertion of the synthetic gene for I-SceI (NdeI-BamHI fragment of pSCM525) under T7 promoter control. This vector is used in strain BL21 (DE3) which expresses the T7 RNA polymerase under IPTG induction.

pSCM351, which is an *E. coli* expression vector derived from pUR291 in which the synthetic gene for I-SceI is fused with the Lac Z gene, producing a hybrid protein.

pSCM353, which is an *E. coli* expression vector derived from pEX1 in which the synthetic gene for I-SceI is fused with the Cro/Lac Z gene, producing a hybrid protein.

Examples of yeast expression vectors are:

pPEX7, which is a yeast expression vector derived from pRP51-Bam O (a LEU2d derivative of pLG-SD5) by insertion of the synthetic gene under the control of the galactose promoter. Expression is induced by galactose.

pPEX408, which is a yeast expression vector derived from pLG-SD5 by insertion of the synthetic gene under the control of the galactose promoter. Expression is induced by galactose.

Figure 7:
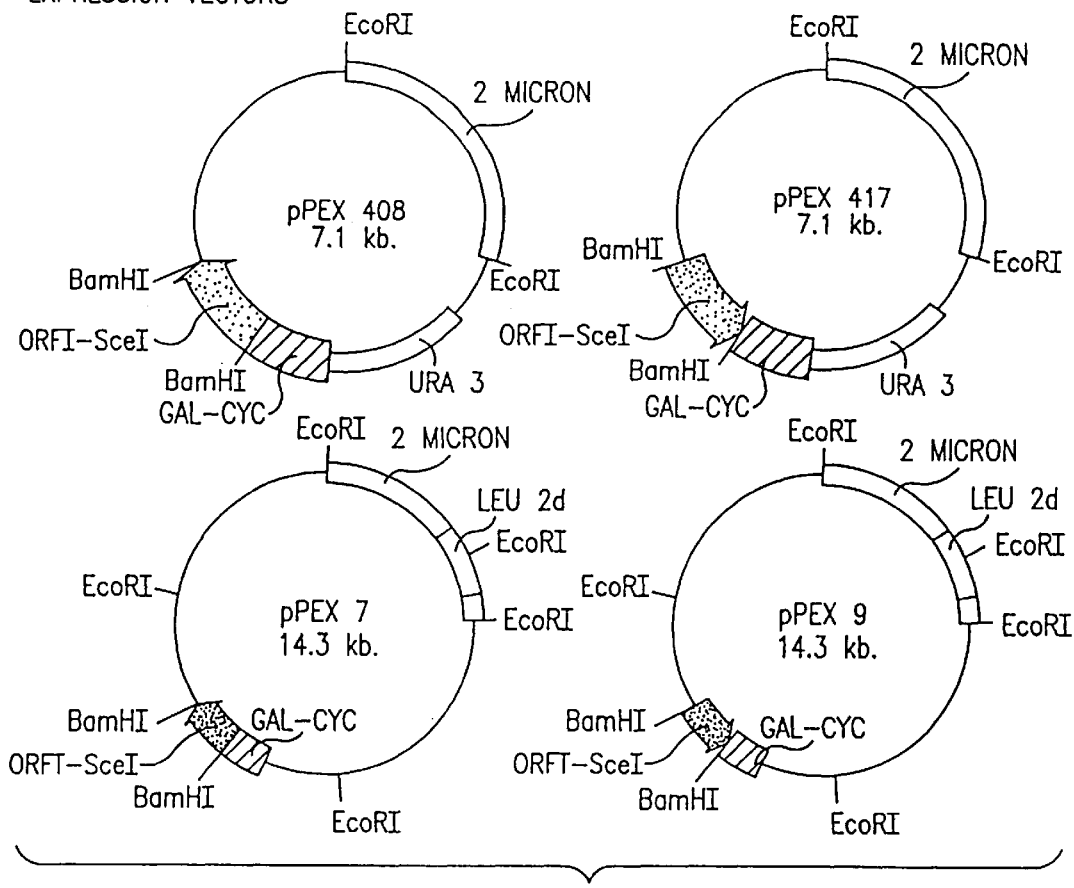
FIG. 7 depicts yeast expression vectors containing the synthetic gene for I-SceI.

Several yeast expression vectors are depicted in FIG. 7.

Figure 8:
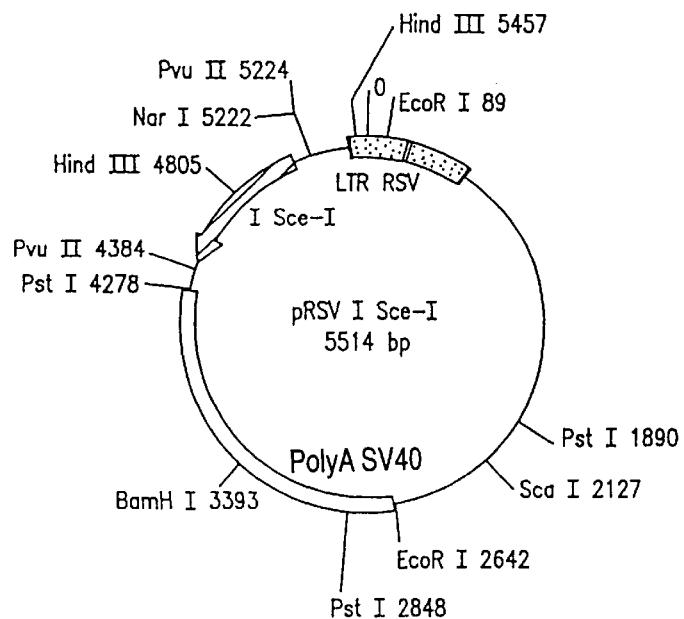
FIG. 8 depicts the mammalian expression vector PRSV I-SceI.

Typical mammalian expression vectors are:

pRSV I-SceI, which is a pRSV derivative in which the synthetic gene (BamHI-PstI fragment from pSCM525) is under the control of the LTR promoter of Rous Sarcoma Virus. This expression vector is depicted in FIG. 8.

Vectors for expression in Chinese Hamster Ovary (CHO) cells can also be employed.

5. Cells Transformed with Vectors of the Invention

The vectors of the invention can be inserted into host organisms using conventional techniques. For example, the vectors can be inserted by transformation, transfection, electroporation, microinjection, or by means of liposomes (lipofection).

Cloning can be carried out in prokaryotic or eukaryotic cells. The host for replicating the cloning vehicle will of course be one that is compatible with the vehicle and in which the vehicle can replicate. Cloning is preferably carried out in bacterial or yeast cells, although cells of fungal, animal, and plant origin can also be employed. The preferred host cells for conducting cloning work are bacterial cells, such as *E. coli*. The use of *E. coli* cells is particularly preferred because most cloning vehicles, such as bacterial plasmids and bacteriophages, replicate in these cells.

In a preferred embodiment of this invention, an expression vector containing the DNA sequence encoding the nucleotide sequence of the invention operatively linked to a promoter is inserted into a mammalian cell using conventional techniques.

Application of I-SceI for Large Scale Mapping

1. Occurrence of Natural Sites in Various Genomes

Using the purified I-SceI enzyme, the occurrence of natural or degenerate sites has been examined on the complete genomes of several species. No natural site was found in *Saccharomyces cerevisiae*, *Bacillus anthracis*, *Borrelia burgdorferi*, *Leptospira biflexa* and *L. interrogans*. One degenerate site was found on T7 phage DNA.

2. Insertion of Artificial Sites

Given the absence of natural I-SceI sites, artificial sites can be introduced by transformation or transfection. Two cases need to be distinguished: site-directed integration by homologous recombination and random integration by non-homologous recombination, transposon movement or retroviral infection. The first is easy in the case of yeast and a few bacterial species, more difficult for higher eucaryotes. The second is possible in all systems.

3. Insertion Vectors

Two types can be distinguished:

1 Site specific cassettes that introduce the I-SceI site together with a selectable marker.

For yeast: all are pAF100 derivatives (Thierry et al. (1990) YEAST 6:521–534) containing the following marker genes:
pAF101: URA3 (inserted in the HindIII site)
pAF103: Neo$^R$ (inserted in BglII site)
pAF104: HIS3 (inserted in BglII site)
pAF105: Kan$^R$ (inserted in BglII site)
pAF106: Kan$^R$ (inserted in BglII site)
pAF107: LYS2 (inserted between HindIII and EcoR V)

Figure 9:
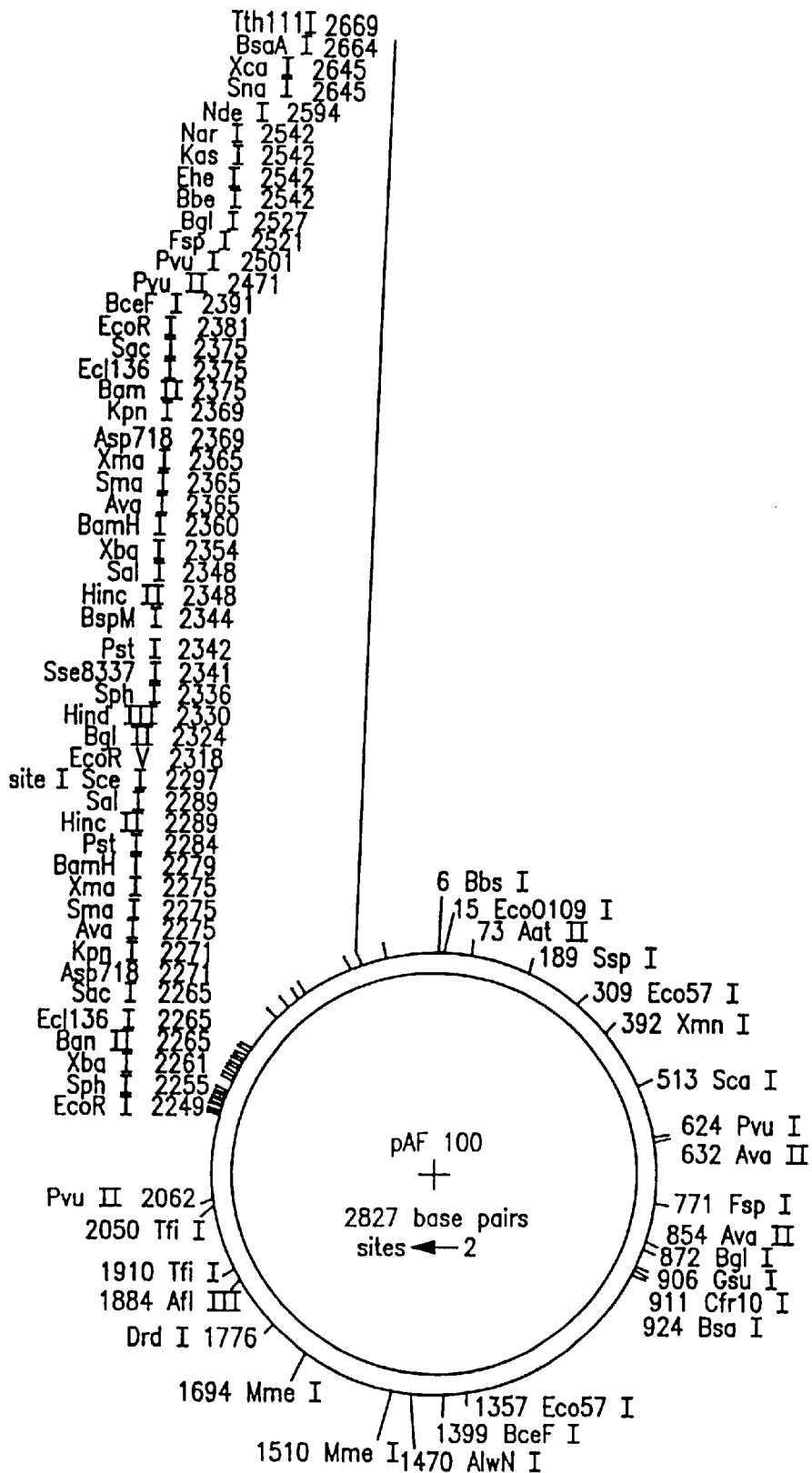
FIG. 9 is a restriction map of the plasmid PAF100. (See also YEAST, 6:521–534, 1990, which is relied upon and incorporated by reference herein).
Figure 10B:
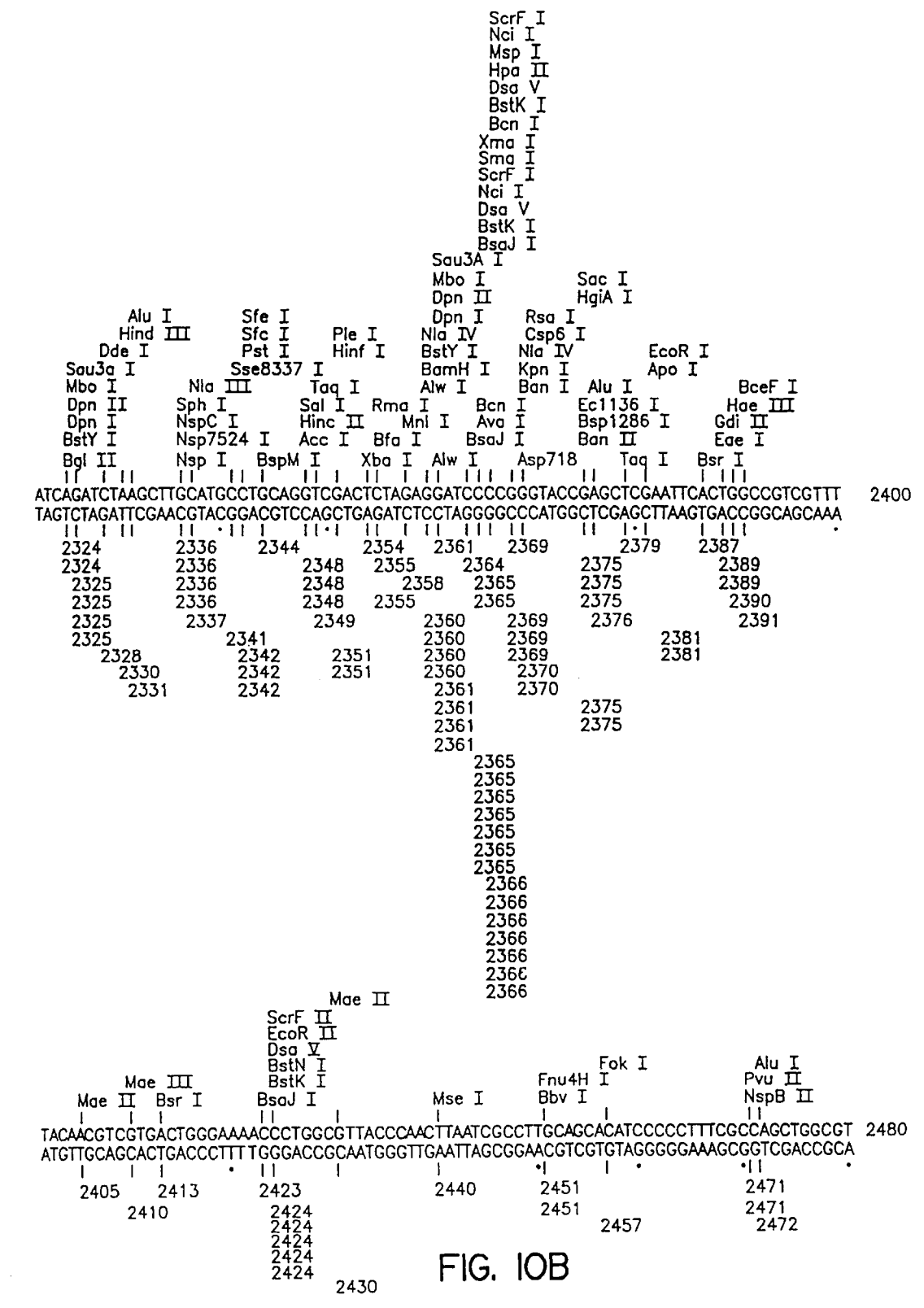

A restriction map of the plasmid pAF100 is shown in FIG. 9. The nucleotide sequence and restriction sites of regions of plasmid pAF100 are shown in FIGS. 10A and 10B. Many transgenic yeast strains with the I-SceI site at various and known places along chromosomes are available.

2 Vectors derived from transposable elements or retroviruses.

Figure 11:
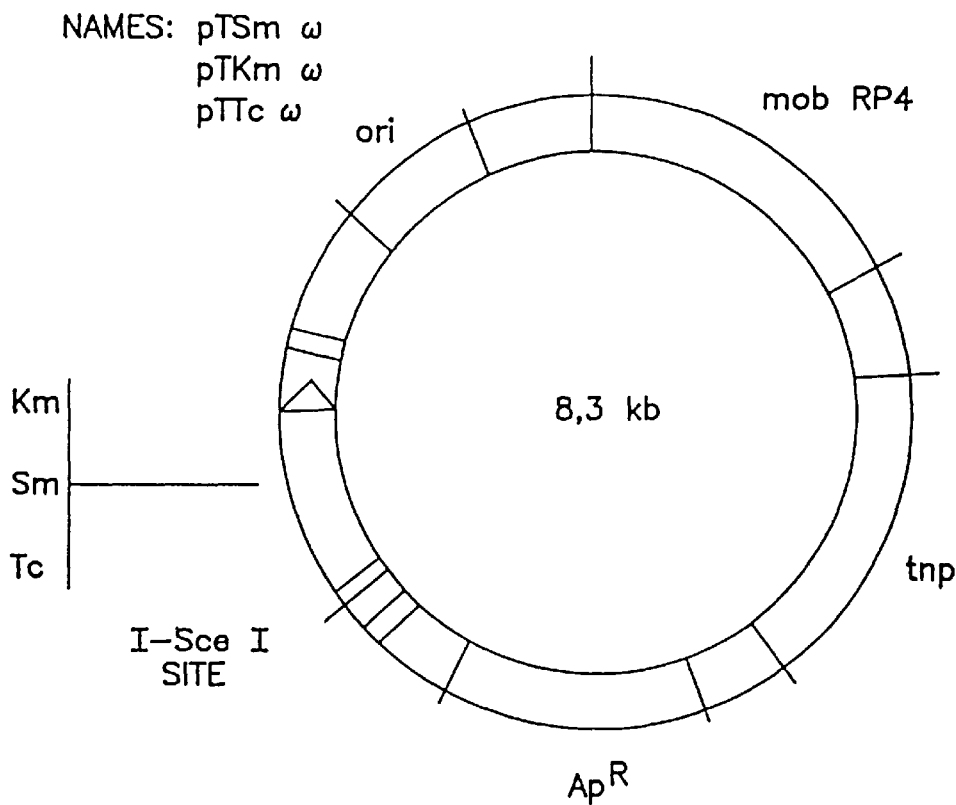
FIG. 11 depicts an insertion vector pTSMω, pTKMω, and pTTcω containing the I-SceI site for E. coli and other bacteria.
Figure 12:
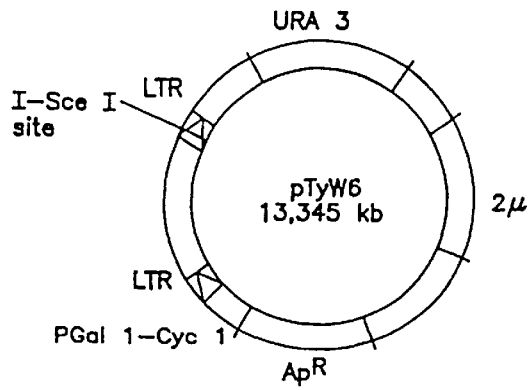
FIG. 12 depicts an insertion vector pTYW6 containing the I-SceI site for yeast.

For *E. coli* and other bacteria: mini Tn5 derivatives containing the I-SceI site and pTSm ω Str$^R$
pTKm ω Kan$^R$     (See FIG. 11)
pTTc ω Tet$^R$ For yeast: pTyω6 is a pD123 derivative in which the I-SceI site has been inserted in the LTR of the Ty element. (FIG. 12)

Figure 13A:
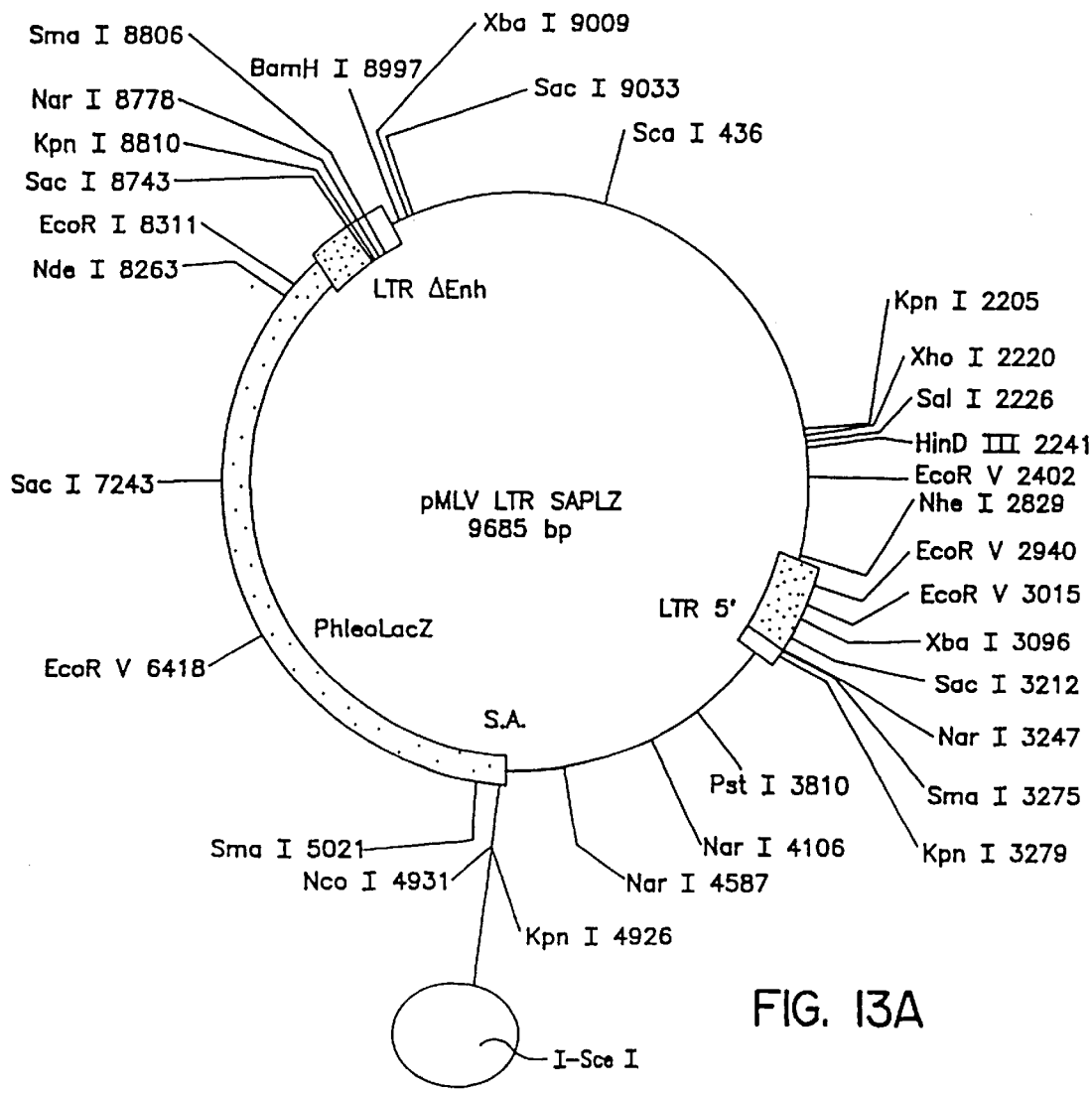

For Mammalian Cells pMLV LTR SAPLZ: containing the I-SceI site in the LTR of MLV and Phleo-LacZ (FIG. 13). This vector is first grown in ψ2 cells (3T3 derivative, from R. Mulligan). Two transgenic cell lines with the I-SceI site at undetermined locations in the genome are available: 1009 (pluripotent nerve cells, J. F. Nicolas) and D3 (ES cells able to generate transgenic animals).

4. The Nested Chromosomal Fragmentation Strategy

The nested chromosomal fragmentation strategy for genetically mapping a eukaryotic genome exploits the unique properties of the restriction endonuclease I-SceI, such as an 18 bp long recognition site. The absence of natural I-SceI recognition sites in most eukaryotic genomes is also exploited in this mapping strategy.

First, one or more I-SceI recognition sites are artificially inserted at various positions in a genome, by homologous recombination using specific cassettes containing selectable markers or by random insertion, as discussed supra. The genome of the resulting transgenic strain is then cleaved completely at the artificially inserted I-SceI site(s) upon incubation with the I-SceI restriction enzyme. The cleavage produces nested chromosomal fragments.

The chromosomal fragments are then purified and separated by pulsed field gel (PFG) electrophoresis, allowing one to "map" the position of the inserted site in the chromosome. If total DNA is cleaved with the restriction enzyme, each artificially introduced I-SceI site provides a unique "molecular milestone" in the genome. Thus, a set of transgenic strains, each carrying a single I-SceI site, can be created which defines physical genomic intervals between the milestones. Consequently, an entire genome, a chromosome or any segment of interest can be mapped using artificially introduced I-SceI restriction sites.

The nested chromosomal fragments may be transferred to a solid membrane and hybridized to a labelled probe containing DNA complementary to the DNA of the fragments. Based on the hybridization banding patterns that are observed, the eukaryotic genome may be mapped. The set of transgenic strains with appropriate "milestones" is used as a reference to map any new gene or clone by direct hybridization.

EXAMPLE 1

Figure 14A:
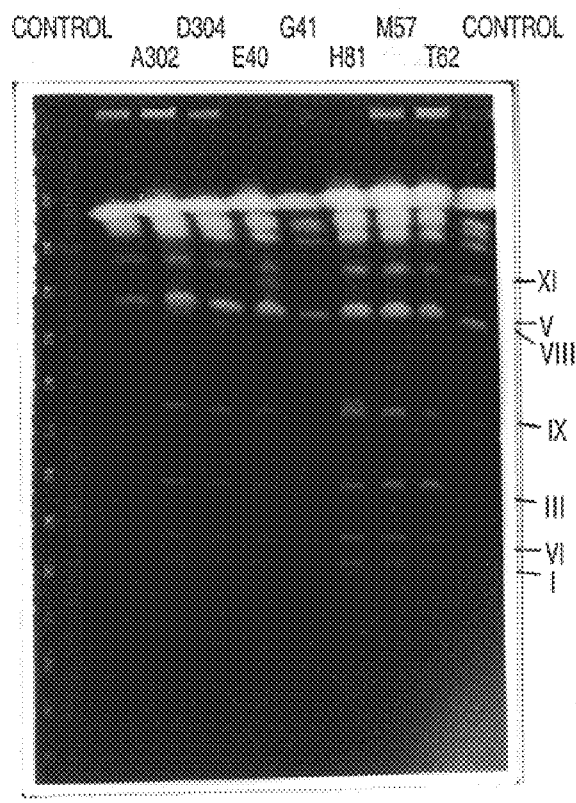
FIG. 14 depicts a set of seven transgenic yeast strains cleaved by I-SceI. Chromosomes from FY1679 (control) and from seven transgenic yeast strains with I-SceI sites inserted at various positions along chromosome XI were treated with I-SceI. DNA was electrophoresed on 1% agarose (SeaKem) gel in 0.25× TBE buffer at 130 V and 12° C. on a Rotaphor apparatus (Biometra) for 70 hrs using 100 sec to 40 sec decreasing pulse times. (A) DNA was stained with ethidium bromide (0.2 μg/ml) and transferred to a Hybond N (Amersham) membrane for hybridization. (B) $^{32}$P labelled cosmid pUKG040 which hybridizes with the shortest fragment of the set was used as a probe. Positions of chromosome XI and shorter chromosomes are indicated.
Figure 14B:
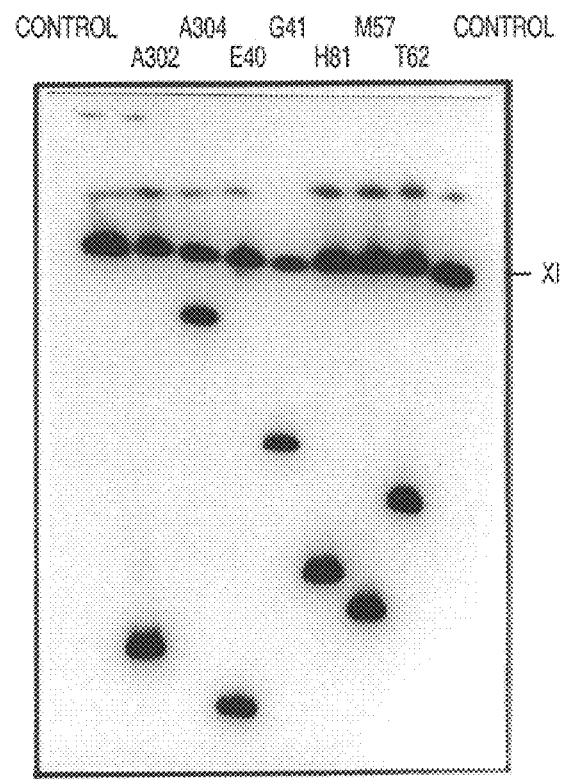
Figure 15A:
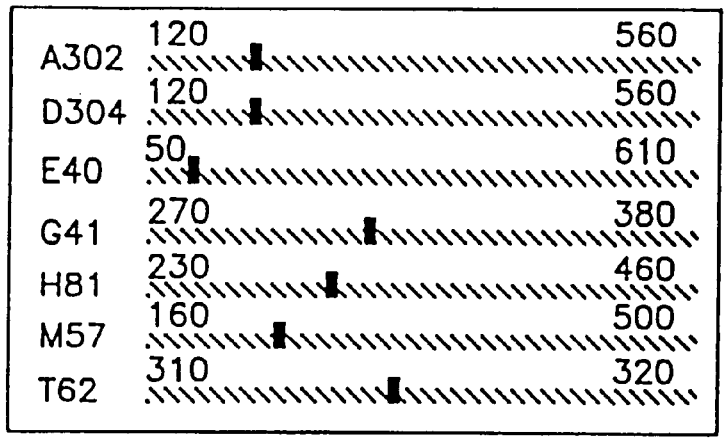
FIG. 15 depicts the rationale of the nested chromosomal fragmentation strategy for genetic mapping. (A) Positions of I-SceI sites are placed on the map, irrespective of the left/right orientation (shorter fragments are arbitrarily placed on the left). Fragment sizes as measured from PFGE (FIG. 14A) are indicated in kb (note that the sum of the two fragment sizes varies slightly due to the limit of precision of each measurement). (B) Hybridization with the probe that hybridizes the shortest fragment of the set determines the orientation of each fragment (see FIG. 14B). Fragments that hybridize with the probe (full lines) have been placed arbitrarily to the left. (C) Transgenic yeast strains have been ordered with increasing sizes of hybridizing chromosome fragments. (D) Deduced I-SceI map with minimal and maximal size of intervals indicated in kb (variations in some intervals are due to limitations of PFGE measurements). (E) Chromosome subfragments are used as probes to assign each cosmid clone to a given map interval or across a given I-SceI site.
Figure 15B:
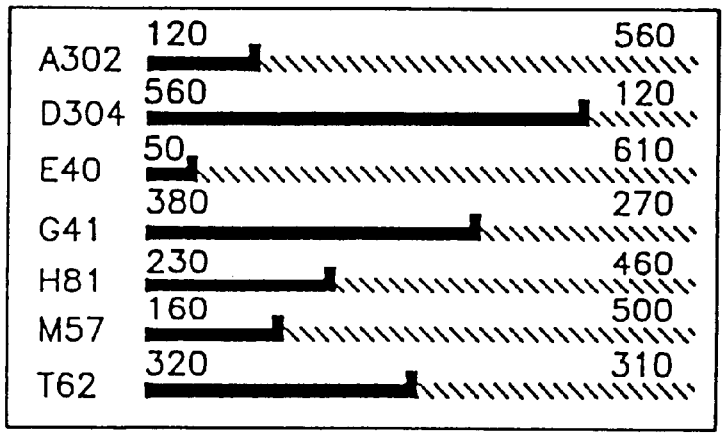
Figure 15C:
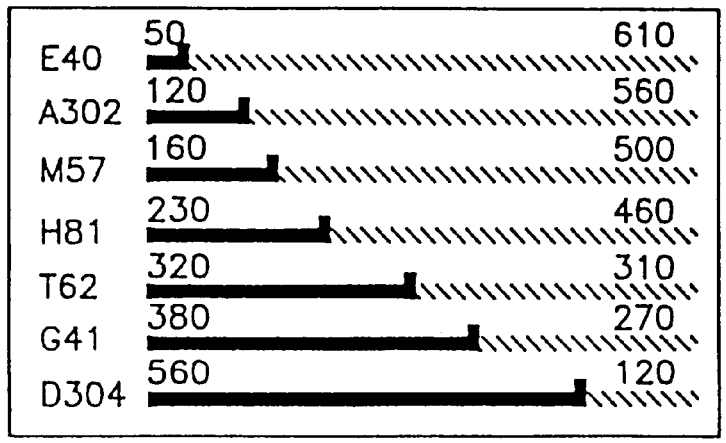

Application of the Nested Chromosomal Fragmentation Strategy to the Mapping of Yeast Chromosome XI This strategy has been applied to the mapping of yeast chromosome XI of *Saccharamyces cerevisiae*. The I-SceI site was inserted at 7 different locations along chromosome XI of the diploid strain FY1679, hence defining eight physical intervals in that chromosome. Sites were inserted from a URA-1-I-SceI cassette by homologous recombination. Two sites were inserted within genetically defined genes, TIF1 and FAS1, the others were inserted at unknown positions in the chromosome from five non-overlapping cosmids of our library, taken at random. Agarose embedded DNA of each of the seven transgenic strains was then digested with I-SceI and analyzed by pulsed field gel electrophoresis (FIGS. 14A). The position of the I-SceI site of each transgenic strain in chromosome XI is first deduced from the fragment sizes without consideration of the left/right orientation of the fragments. Orientation was determined as follows. The most telomere proximal I-SceI site from this Bet of strains is in the transgenic E40 because the 50 kb fragment is the shortest of all fragments (FIG. 15A). Therefore, the cosmid clone pUKGO40, which was used to insert the I-SceI site in the transgenic E40, is now used as a probe against all chromosome fragments (FIG. 14B). As expected, pUKG040 lights up the two fragments from strain E40 (50 kb and 630 kb, respectively). The large fragment is close to the entire chromosome XI and shows a weak hybridization signal due to the fact that the insert of pUKG040, which is 39 kb long, contains less than 4 kb within the large chromosome fragment. Note that the entire chromosome XI remains visible after I-SceI digestion, due to the fact that the transgenic strains are diploids in which the I-SceI site is inserted in only one of the two homologs. Now, the pUKG040 probe hybridizes to only one fragment of all other transgenic strains allowing unambiguous left/right orientation of I-SceI sites (See FIG. 15B). No significant cross hybridization between the cosmid vector and the chromosome subfragment containing the I-SceI site insertion vector is visible. Transgenic strains can now be ordered such that I-SceI sites are located at increasing distances from the hybridizing end of the chromosome (FIG. 15C) and the I-SceI map can be deduced (FIG. 15D).

Precision of the mapping depends upon PFGE resolution and optimal calibration. Note that actual left/right orientation of the chromosome with respect to the genetic map is not known at this step. To help visualize our strategy and to obtain more precise measurements of the interval sizes between I-SceI sites between I-SceI, a new pulsed field gel electrophoresis with the same transgenic strains now placed in order was made (FIG. 16). After transfer, the fragments were hybridized successively with cosmids pUKG040 and pUKG066 which light up, respectively, all fragments from the opposite ends of the chromosome (clone pUKG066 defines the right end of the chromosome as defined from the genetic map because it contains the SIR1 gene. A regular stepwise progression of chromosome fragment sizes is observed. Note some cross hybridization between the probe pUKG066 and chromosome III, probably due to some repetitive DNA sequences.

Figures 15D, 15E:
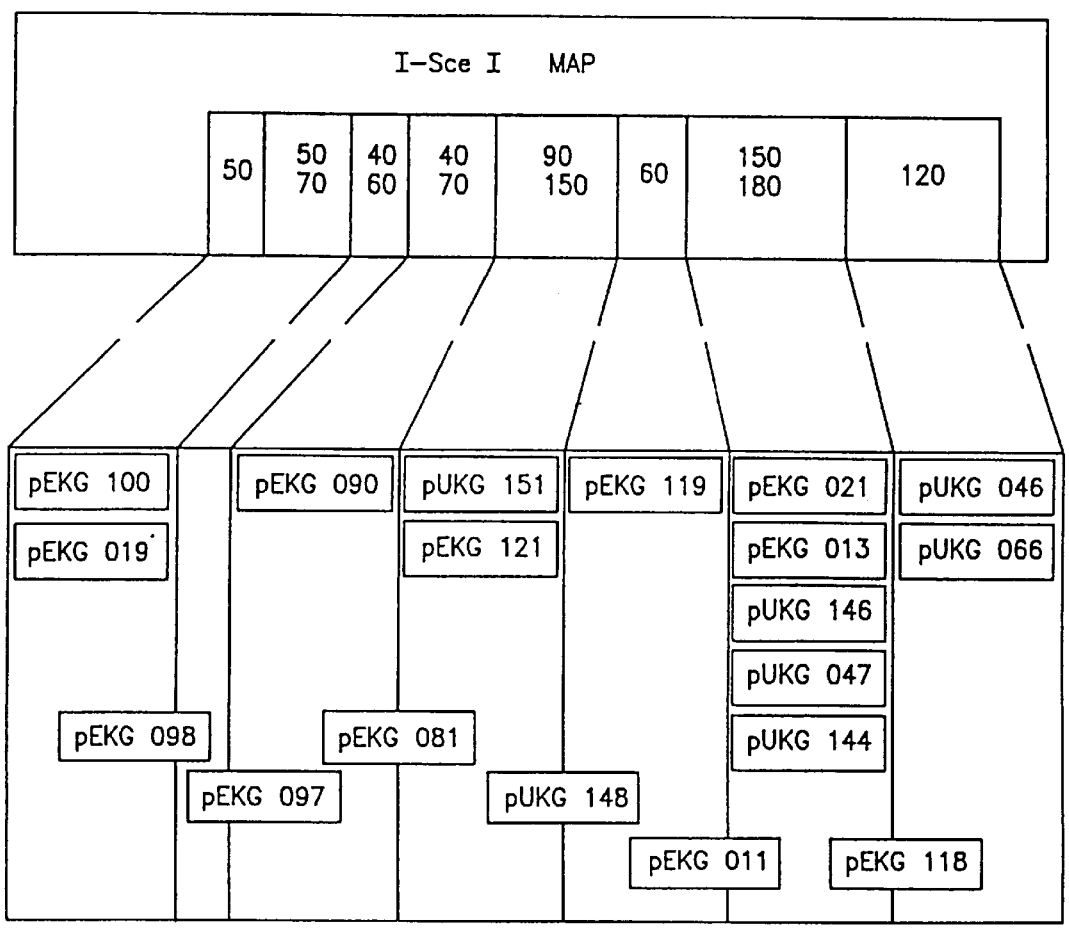

All chromosome fragments, taken together, now define physical intervals as indicated in FIG. 15d. The I-SceI map obtained has an 80 kb average resolution.

EXAMPLE 2

Application of the Nested Chromosomal Fragmentation Strategy to the Mapping of Yeast Artificial Chromosome (YAC) Clones This strategy can be applied to YAC mapping with two possibilities.

1 insertion of the I-SceI site within the gene of interest using homologous recombination in yeast. This permits mapping of that gene in the YAC insert by I-SceI digestion in vitro. This has been done and works.

2 random integration of I-SceI sites along the YAC insert by homologous recombination in yeast using highly repetitive sequences (e.g., B2 in mouse or Alu in human). Transgenic strains are then used as described in ref. P1 to sort libraries or map genes.

The procedure has now been extended to YAC containing 450 kb of Mouse DNA. To this end, a repeated sequence of mouse DNA (called B2) has been inserted in a plasmid containing the I-SceI site and a selectable yeast marker (LYS2). Transformation of the yeast cells containing the recombinant YAC with the plasmid linearized within the B2 sequence resulted in the integration of the I-SceI site at five different locations distributed along the mouse DNA insert. Cleavage at the inserted I-SceI sites using the enzyme has been successful, producing nested fragments that can be purified after electrophoresis. Subsequent steps of the protocol exactly parallels the procedure described in Example 1.

EXAMPLE 3

Application of Nested Chromosomal Fragments to the Direct Sorting of Cosmid Libraries The nested, chromosomal fragments can be purified from preparative PFG and used as probes against clones from a chromosome X1 specific sublibrary. This sublibrary is composed of 138 cosmid clones (corresponding to eight times coverage) which have been previously sorted from our complete yeast genomic libraries by colony hybridization with PFG purified chromosome X1. This collection of unordered clones has been sequentially hybridized with chromosome fragments taken in order of increasing sizes from the left end of the chromosomes Localization of each cosmid clone on the I-SceI map could be unambiguously determined from such hybridizations. To further verify the results and to provide a more precise map, a subset of all cosmid clones, now placed in order, have been digested with EcoRI, electrophoresed and hybridized with the nested series of chromosome fragments in order of increasing sizes from the left end of the chromosome. Results are given in FIG. 17.

Figure 17C:
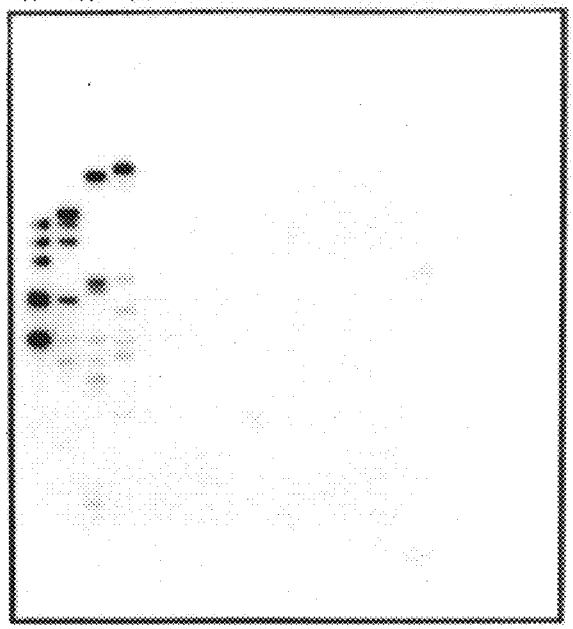
FIG. 17 depicts mapping of a cosmid collection using the nested chromosomal fragments as probes. Cosmid DNAs were digested with EcoRI and electrophoresed on 0.9% agarose (SeaKem) gel at 1.5 V/cm for 14 hrs, stained with ethidium bromide and transferred to a Hybond N membrane. Cosmids were placed in order from previous hybridizations to help visualize the strategy. Hybridizations were carried out serially on three identical membranes using left end nested chromosome fragments purified on PFGE (see FIG. 16) as probes. A: ethidium bromide staining (ladder is the BRL "1 kb ladder"), B: membrane #1, probe: Left tel to A302 site, C: membrane #1, probe: Left tel to M57 site, D: membrane #2, probe: Left tel to H81 site, E: membrane #2, probe: Left tel to T62 site, F: membrane #3, probe: Left tel to G41 site, G: membrane #3, probe: Left tel to D304 site, H: membrane #3, probe: entire chromosome XI.
Figure 17D:
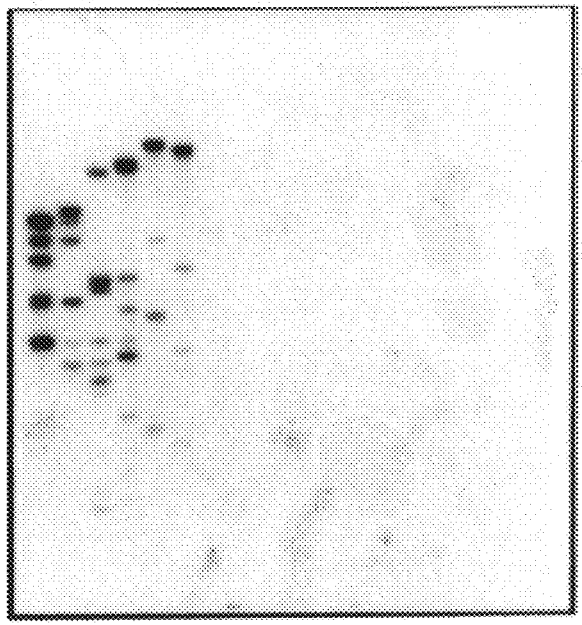
Figure 17E:
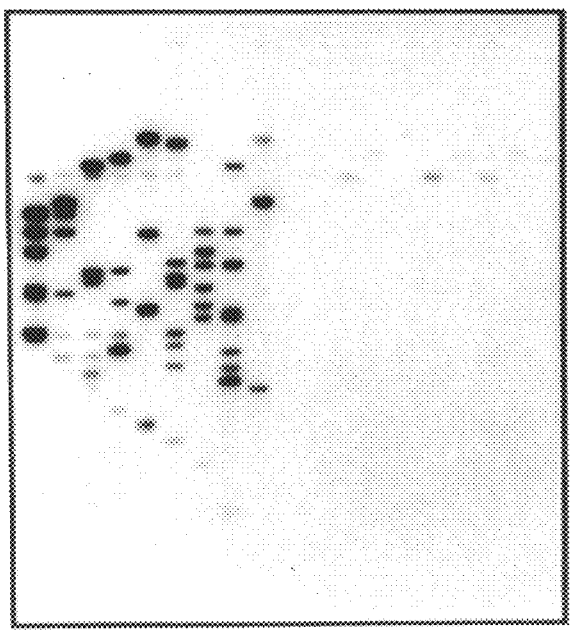
Figure 17F:
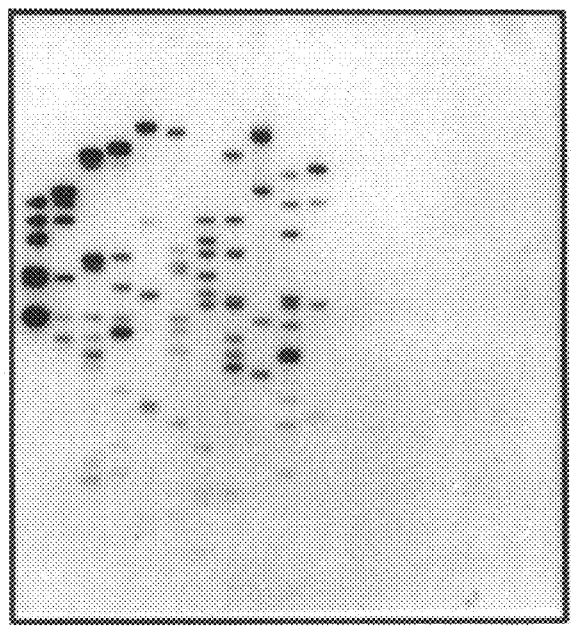
Figure 17G:
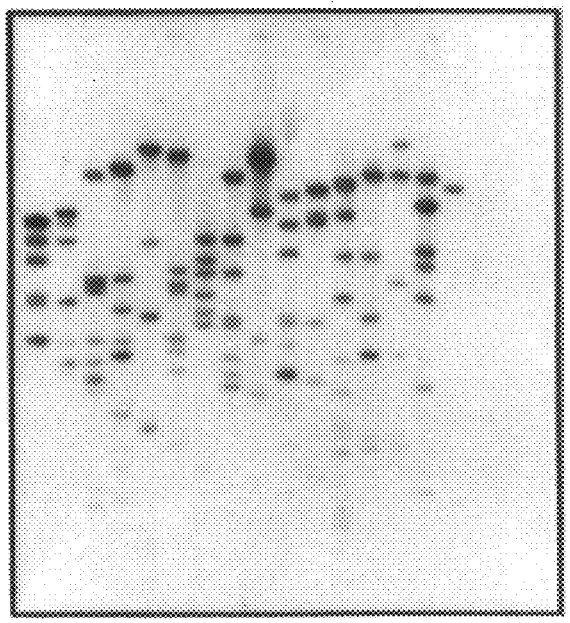
Figure 17H:
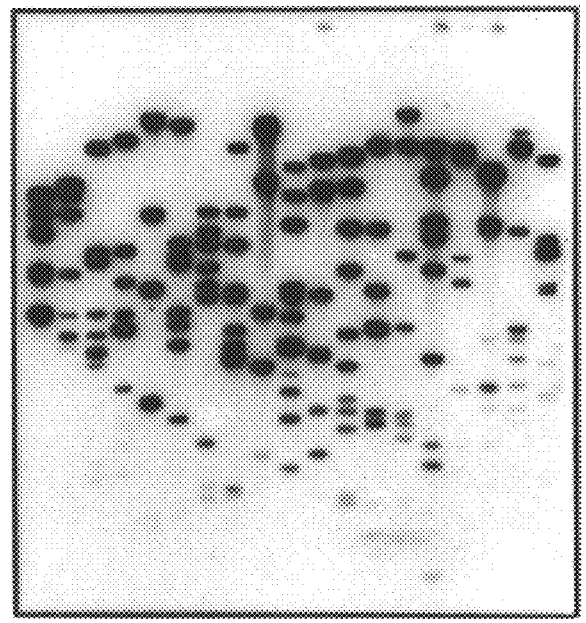

For a given probe, two cases can be distinguished: cosmid clones in which all EcoRI fragments hybridize with the probe and cosmid clones in which only some of the EcoRI fragments hybridize (i.e., compare pEKG100 to pEKG098 in FIG. 17b). The first category corresponds to clones in which the insert is entirely included in one of the two chromosome fragments, the second to clones in which the insert overlaps an I-SceI site. Note that, for clones of the pEKG series, the EcoRI fragment of 8 kb is entirely composed of vector sequences (pWE15) that do not hybridize with the chromosome fragments. In the case where the chromosome fragment possesses the integration vector, a weak cross hybridization with the cosmid is observed (FIG. 17e).

Figure 18:
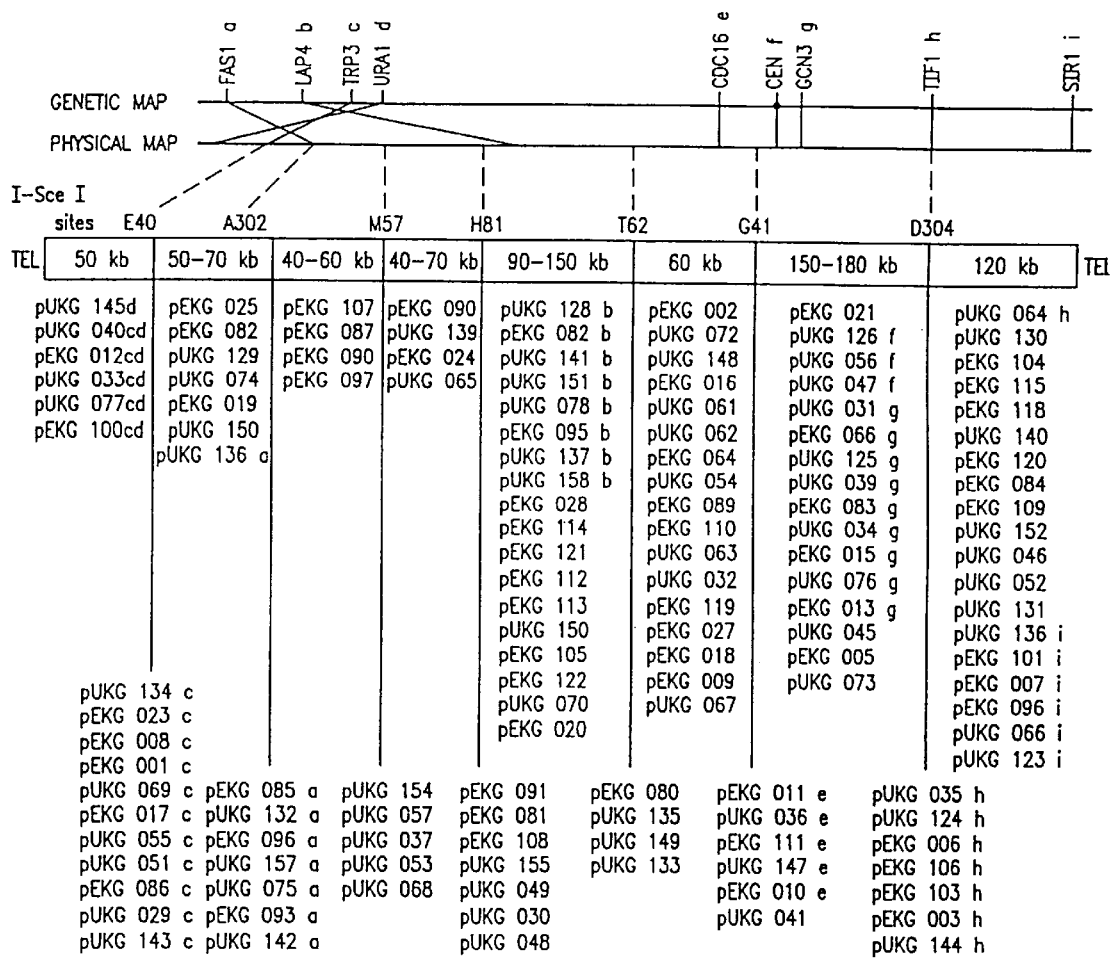
FIG. 18 depicts a map of the yeast chromosome XI as determined from the nested chromosomal fragmentation strategy. The chromosome is divided into eight intervals (with sizes indicated in kb, see FIG. 15D) separated by seven I-SceI sites (E40, A302 . . . ). Cosmid clones falling either within intervals or across a given I-SceI site are listed below intervals or below interval boundaries, respectively. Cosmid clones that hybridize with selected genes used as probes are indicated by letters (a–i). They localize the gene with respect to the I-SceI map and allow comparison with the genetic map (top).

Examination of FIG. 17 shows that the cosmid clones can unambiguously be ordered with respect to the I-SceI map (FIG. 13E), each clone falling either in a defined interval or across an I-SceI site. In addition, clones from the second category allow us to place some EcoRI fragments on the I-SceI maps, while others remain unordered. The complete set of chromosome XI- specific cosmid clones, covering altogether eight times the equivalent of the chromosome, has been sorted with respect to the I-SceI map, as shown in FIG. 18.

5. Partial Restriction Mapping Using I-SceI

In this embodiment, complete digestion of the DNA at the artificially inserted I-SceI site is followed by partial digestion with bacterial restriction endonucleases of choice. The restriction fragments are then separated by electrophoresis and blotted. Indirect end labelling is accomplished using left or right I-Sce half sites. This technique has been successful with yeast chromosomes and should be applicable without difficulty for YAC.

Partial restriction mapping has been done on yeast DNA and on mammalian cell DNA using the commercial enzyme I-SceI. DNA from cells containing an artificially inserted I-SceI site is first cleaved to completion by I-SceI. The DNA is then treated under partial cleavage conditions with bacterial restriction endonucleases of interest (e.g., BamHI) and electrophoresed along with size calibration markers. The DNA is transferred to a membrane and hybridized successively using the short sequences flanking the I-SceI sites on either side (these sequences are known because they are part of the original insertion vector that was used to introduce the I-SceI site). Autoradiography (or other equivalent detection system using non radioactive probes) permit the visualization of ladders, which directly represent the succession of the bacterial restriction endonuclease sites from the I-SceI site. The size of each band of the ladder is used to calculate the physical distance between the successive bacterial restriction endonuclease sites.

Application of I-SceI For In Vivo Site Directed Recombination

1. Expression of I-SceI in Yeast

The synthetic I-SceI gene has been placed under the control of a galactose inducible promoter on multicopy plasmids pPEX7 and pPEX408. Expression is correct and induces effects on site as indicated below. A transgenic yeast with the I-SceI synthetic gene inserted in a chromosome under the control of an inducible promoter can be constructed.

2. Effects of Site Specific Double Strand Breaks in Yeast (Refs. 18 and P4)

Effects on Plasmid-Borne I-SceI Sites

Intramolecular effects are described in detail in Ref. 18. Intermolecular (plasmid to chromosome) recombination can be predicted.

Effects on Chromosome Integrated I-SceI Sites

In a haploid cell,-a single break within a chromosome at an artificial I-SceI site results in cell division arrest followed by death (only a few % of survival). Presence of an intact sequence homologous to the cut site results in repair and 100% cell survival. In a diploid cell, a single break within a chromosome at an artificial I-SceI site results in repair using the chromosome homolog and 100% cell survival. In both cases, repair of the induced double strand break results in loss of heterozygosity with deletion of the non homologous sequences flanking the cut and insertion of the non homologous sequences from the donor DNA molecule.

3. Application For In Vivo Recombination YACs in Yeast

Construction of a YAC vector with the I-SceI restriction site next to the cloning site should permit one to induce homologous recombination with another YAC if inserts are partially overlapping. This is useful for the construction of contigs.

4. Prospects For Other Organisms

Insertion of an I-SceI restriction site has been done for bacteria (*E. coli, Yersinia entorocolitica, Y. pestis, Y. pseudotuberculosis*), and mouse cells. Cleavage at the artificial I-SceI site in vitro has been successful with DNA from the transgenic mouse cells. Expression of I-SceI from the synthetic gene in mammalian or plant cells should be successful.

The I-SceI site has been introduced in mouse cells and bacterial cells as follows:

1 Mouse cells:
   a Mouse cells ($\Omega 2$) were transfected with the DNA of the vector PMLV LTR SAPLZ containing the I-SceI site using standard calcium phosphate transfection technique.
   b Transfected cells were selected in DMEM medium containing phleomycin with 5% fetal calf serum and grown under 12% $CO_2$, 100% humidity at 37° C. until they form colonies.
   c Phleomycin resistant colonies were subcloned once in the same medium.

d Clone MLOP014, which gave a titer of $10^5$ virus particles per ml, was chosen. This clone was deposited at C.N.C.M. on May 5, 1992 under culture collection accession No. I-1207.

e The supernatant of this clone was used to infect other mouse cells (1009) by spreading $10^5$ virus particles on $10^5$ cells in DMEM medium with 10% fetal calf serum and 5 mg/ml of "polybrain". Medium was replaced 6 hours after infection by the same fresh medium.

f 24 hours after infection, phleomycin resistant cells were selected in the same medium as above.

g phleomycin resistant colonies were subcloned once in the same medium.

h one clone was picked and analyzed. DNA was purified with standard procedures and digested with I-SceI under optimal conditions.

2 Bacterial cells:

Mini Tn 5 transposons containing the I-SceI recognition site were constructed in *E. coli* by standard recombinant DNA procedures. The mini Tn 5 transposons are carried on a conjugative plasmid. Bacterial conjugation between *E. coli* and Yersinia is used to integrate the mini Tn 5 transposon in Yersinia. Yersinia cells resistant to Kanamycin, Streptomycin or tetracycline are selected (vectors pTKM-ω, pTSM-ω and pTTc-ω, respectively).

Several strategies can be attempted for the site specific insertion of a DNA fragment from a plasmid into a chromosome. This will make it possible to insert transgenes at predetermined sites without laborious screening steps. Strategies are:

1 Construction of a transgenic cell in which the I-SceI recognition site is inserted at a unique location in a chromosome. Cotransformation of the transgenic cell with the expression vector and a plasmid containing the gene of interest and a segment homologous to the sequence in which the I-SceI site is inserted.

2 Insertion of the I-SceI recognition site next to or within the gene of interest carried on a plasmid. Cotransformation of a normal cell with the expression vector carrying the synthetic I-SceI gene and the plasmid containing the I-SceI recognition site.

3 Construction of a stable transgenic cell line in which the I-SceI gene has been integrated in the genome under the control of an inducible or constitutive cellular promoter. Transformation of the cell line by a plasmid containing the I-SceI site next to or within the gene of interest.

Site Directed Homologous Recombination

Figure 19A:
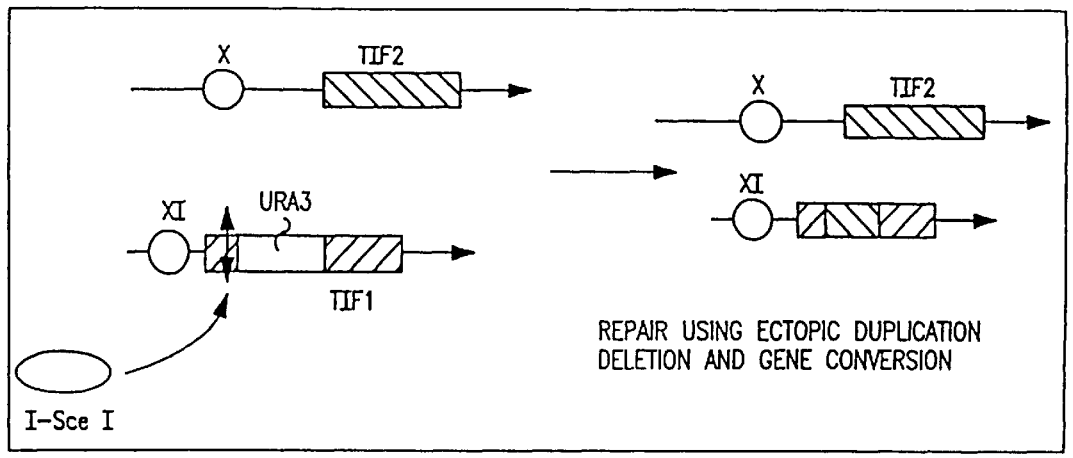
FIGS. 19A and 19B depict diagrams of successful site directed homologous recombination experiments performed in yeast.
Figure 19B:
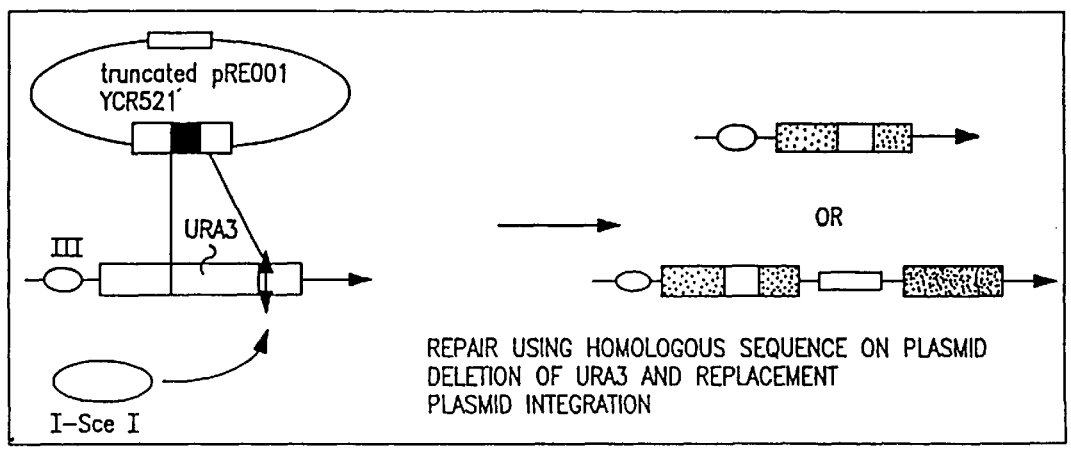

Diagrams of successful experiments performed in yeast are given in FIG. 19.

Publications Cited in Application

1. B. Dujon, Sequence of the intron and flanking exons of the mitochondrial 21 S rRNA gene of yeast strains having different alleles at the w and RIB 1 loci. Cell (1980) 20, 185–187.
2. F. Michel, A. Jacquier and B. Dujon, Comparison of fungal mitochondrial introns reveals extensive homologies in RNA secondary structure. Biochimie, 1982, 64, 867–881.
3. F. Michel and B. Dujon, Conservation of RNA secondary structures in two intron families including mitochondrial-, chloroplast-, and nuclear-encoded members. The EMBO Journal, 1983, 2, 33–38.
4. A. Jacquier and B. Dujon, The intron of the mitochondrial 21S rRNA gene: distribution in different yeast species and sequence comparison between *Kluyveromyces thermotolerans* and *Saccharomyces cerevisiae*. Mol. Gen. Gent. (1983) 192, 487–499.
5. B. Dujon and A. Jacquier, Organization of the mitochondrial 21S rRNA gene in *Saccharomyces cerevisiae:* mutants of the peptidyl transferase centre and nature of the omega locus in "Mitochondria 1983", Editors R. J. Schweyen, K. Wolf, F. Kaudewitz, Walter de Gruyter et Co., Berlin, New York (1983), 389–403.
6. A. Jacquier and B. Dujon, An intron encoded protein is active in a gene conversion process that spreads an intron into a mitochondrial gene. Cell (1985) 41, 383–394.
7. B. Dujon, G. Cottarel, L. Colleaux, M. Betermier, A. Jacquier, L. D'Auriol, F. Galibert, Mechanism of integration of an intron within a mitochondrial gene: a double strand break and the transposase function of an intron encoded protein as revealed by in vivo and in vitro assays. In Achievements and perspectives of Mitochondrial Research". Vol. II, Biogenesis, E. Quagliariello et al. Eds. Elsevier, Amsterdam (1985) pages 215–225.
8. L. Colleaux, L. D'Auriol, M. Betermier, G. Cottarel, A. Jacquier, F. Galibert, and B. Dujon, A universal code equivalent of a yeast mitochondrial intron reading frame is expressed into *Escherichia coli* as a specific double strand endonuclease. Cell (1986) 44, 521–533.
9. B. Dujon, L. Colleaux, A. Jacquier, F. Michel and C. Monteilhet, Mitochondrial introns as mobile genetic elements: the role of intron-encoded proteins. In "Extrachromosomal elements in lower eucaryotes", Reed B et al. Eds. (1986) Plenum Pub. Corp. 5–27.
10. F. Michel and B. Dujon, Genetic Exchanges between Bacteriophage T4 and Filamentous Fungi? Cell (1986) 46, 323.
11. L. Colleaux, L. D'Auriol, F. Galibert and B. Dujon, Recognition and cleavage site of the intron encoded omega transposase. PNAS (1988), 85, 6022–6026.
12. B. Dujon, Group I introns as mobile genetic elements, facts and mechanistic speculations: A Review. Gene (1989), 82, 91–114.
13. B. Dujon, M. Belfort, R. A. Butow, C. Jacq, C. Lemieux, P. S. Perlman, V. M. Vogt, Mobile introns: definition of terms and recommended nomenclature. Gene (1989), 82, 115–118.
14. C. Monteilhet, A. Perrin, A. Thierry, L. Colleaux, B. Dujon, Purification and Characterization of the in vitro activity of I-SceI, a novel and highly specific endonuclease encoded by a group I intron. Nucleic Acid Research (1990), 18, 1407–1413.
15. L. Colleaux, M-R. Michel-Wolwertz, R. F. Matagne, B. Dujon—The apocytochrome b gene of *Chlamydomonas smithii* contains a mobile intron related to both Saccharomyces and Neurospora introns. Mol. Gen. Genet. (1990) 223, 288–296.
16. B. Dujon Des introns autonomes et mobiles. Annales de l'Institut Pasteur/Actualites (1990) 1. 181–194.
17. A. Thierry, A. Perrin, J. Boyer, C. Fairhead, B. Dujon, B. Frey, G. Schmitz. Cleavage of yeast and bacteriophage 17 genomes at a single site using the rare cutter endonuclease I-Sce. I Nuc. Ac. Res. (1991) 19, 189–190.
18. A. Plessis, A. Perrin, J. E. Haber, B. Dujon, Site specific recombination determined by I-SceI, a mitochondrial intron-encoded endonuclease expressed in the yeast nucleus. GENETICS (1992) 130, 451–460.

Abstracts

A1. A. Jacquier, B. Dujon. Intron recombinational insertion at-the DNA level: Nature of a specific receptor site and direct role of an intron encoded protein. Cold Spring Harbor Symposium 1984.

A2. I. Colleaux, L. D'Auriol, M. Demariaux, B. Dujon, F. Galibert, and A. Jacquier, Construction of a universal code equivalent from a mitochondrial intron encoded transposase gene using oligonucleotide directed multiple mutagenesis. Colloque International de DNRS "oligonucleotids et Genetique Moleculaire" Aussois (Savoie) Jan. 8–12, 1985.

A3. L. Colleaux, D'Auriol, M. Demariaux, B. Dujon, F. Galibert, and A. Jacquier, Expression in *E. coli* of a universal code equivalent of a yeast mitochondrial intron reading frame involved in the integration of an intron within a gene. Cold Spring Harbor Meeting on "Molecular Biology of Yeast", Aug. 13–19, 1985.

A4. B. Dujon, G. Cottarel, L. Colleaux, M. Demariaux, A. Jacquier, L. D'Auriol, and F. Galibert, Mechanism of integration of an intron within a mitochondrial gene: a double strand break and the "transposase" function of an intron encoded protein as revealed by in vivo and in vitro assays. International symposium on "Achievements and Perspectives in Mitochondrial Research", Selva de Fasono (Brindisi, Italy) Sep. 26, 1985.

A5. L. Colleaux, G. Cottarel, M. Betermier, A. Jacquier, B. Dujon, L. D'auriol, and F. Galibert, Mise en evidence de l'activite endonuclease double brin d'unc protein codee par un intron mitochondrial de levure. Forum sur la Biologie Moleculaire de la levure, Bonbannes, France Oct. 2–4, 1985.

A6. B. Dujon, L. Colleaux, F. Michel and A. Jacquier, Mitochondrial introns as mobile genetic elements. In "Extrachromosomal elements in lower eucaryotes", Urbana, Ill., Jun. 1–5, 1986.

A7. L. Colleaux and B. Dujon, Activity of a mitochondrial intron encoded transposase. Yeast Genetics and Molecular Biology Meeting, Urbana, Ill., Jun. 3–6, 1986.

A8. L. Colleaux and B. Dujon, The role of a mitochondrial intron encoded protein. XIIIth International Conference on Yeast Genetics and Molecular Biology, Banff, Alberta (Canada) Aug. 31–Sep. 5, 1986.

A9. L. Colleaux, L. D'Aurio, F. Galibert and and B. Dujon, Recognition and cleavage specificity of an intron encoded transposase. 1987 Meeting on Yeast Genetics and Molecular Biology. San Francisco, Calif. Jun. 16–21, 1987.

A10. A. Perrin, C. Monteilhet, L. Colleaux and B. Dujon, Biochemical activity of an intron encoded transposase of *Saccharomyces cerevisiae*. Cold Spring Harbor Meeting on "Molecular Biology of Mitochondria and chloroplasts" Aug. 25–30, 1987 Cold Spring Harbor, N.Y.

A11. B. Dujon, A. Jacquier, L. Colleaux, C. Monteilhet, A. Perrin, "Les Introns autoepissables et leurs proteins" Colloque "Biologie Moleculaire de la levure: expression genetique chez Saccharomyces "organise par la Societe francaise de Microbiologie Jan. 18, 1988 Institut Pasteur, Paris.

A12. L. Colleaux, L. D'Auriol, C. Monteilhet, F. Galibert and B. Dujon, Characterization of the biochemical activity of an intron encoded transposase. 14th International Conference on Yeast Genetics and Molecular Biology. Espoo, Finland, Aug. 7–13, 1988.

A13. B. Dujon, A goup I intron as a mobile genetic element, Albany Conference sur "RNA: catalysis, splicing, evolution", Albany, N.Y., Sep. 22–25, 1988.

A14. B. Dujon, L. Colleaux, C. Monteilhet, A. Perrin, L. D'Auriol, F. Galibert, Group I introns as mobile genetic elements: the role of intron encoded proteins and the nature of the target site. 14th Annual EMBO Symposium "Organelle genomes and the nucleus" Heidelberg, Sep. 26–29, 1988.

A15. L. Colleaux, R. Matagne, B. Dujon, A new mobile mitochondrial intron provides evidence for genetic exchange between Neurospora and Chlamydomonas species. Cold Spring Harbor, May 1989.

A16. L. Colleaux, M. R. Michel-Wolwertz, R. F. Matagne, B. Dujon, The apoxytochrome b gene of Chlamydomonas smithii contains a mobile intron related to both Saccharomyces and Neurospora introns. Fourth International Conference on Cell and Molecular Biology of Chlamydomonas. Madison, Wis., April 1990.

A17. B. Dujon, L. Colleaux, E. Luzi, C. Monteilhet, A. Perrin, A. Plessis, I. Stroke, A. Thierry, Mobile Introns, EMBO Workshop on "Molecular Mechanisms of transposition and its control, Roscoff (France) June 1990.

A18. A. Perrin, C. Monteilhet, A. Thierry, E. Luzi, I. Stroke, L. Colleaux, B. Dujon. I-SceI, a novel double strand site specific endonuclease, encoded by a mobile group I intron in Yeast. Workshop on "RecA and Related Proteins" Sacly, France Sep. 17–21 1990.

A19. A. Plessis, A. Perrin, B. Dujon, Site specific recombination induced by double strand endonucleases, HO and I-SceI in yeast. Workshop on "RecA and Related Proteins" Saclay, France Sep. 17–21, 1990.

A20. B. Dujon, The genetic propagation of introns 20th FEBS Meeting, Budapest, Hungary, August 1990.

A21. E. Luzi, B. Dujon, Analysis of the intron encoded site specific endonuclease I-SceI by mutagenesis, Third European Congress on Cell Biology, Florence, Italy, September 1990.

A22. B. Dujon, Self splicing introns as contagious genetic elements. Journees Franco-Beiges de Pont a Mousson. October 1990.

A23. B. Frey, H. Dubler, G. Schmitz, A. Thierry, A. Perrin, J. Boyer, C. Fairhead, B. Dujon, Specific cleavage of the yeast genome at a single site using the rare cutter endonuclease I-SceI Human Genome, Frankfurt, Germany, November 1990.

A24. B. Dujon, A. Perrin, I. Stroke, E. Luzi, L. Colleaux, A. Plessis, A. Thierry, The genetic mobility of group I introns at the DNA level. Keystone Symposia Meeting on "Molecular Evolution of Introns and Other RNA elements", Taos, N.M. Feb. 2–8, 1991.

A25. B. Dujon, J. Boyer, C. Fairhead, A. Perrin, A Thierry, Cartographie chez la levure. Reunion "Strategies d'etablissement des cartes geniques" Toulouse 30–31 Mai 1991.

A26. B. Dujon, A. Thierry, Nested chromosomal fragmentation using the meganuclease I-SceI: a new method for the rapid mapping of the yeast genome. Elounda, Crete 15–17 Mail 1991.

A27. A. Thierry, L. Gaillon, F. Galibert, B. Dujon. The chromosome XI library: what has been accomplished, what is left. Brugge meeting Sep. 22–24, 1991.

A28. B. Dujon, A. Thierry, Nested chromosomal fragmentation using the meganuclease I-SceI: a new method for the rapid physical mapping of the eukaryotic genomes. Cold Spring Harbor May 6–10, 1992.

A29. A. Thierry, L. Gaillon, F. Galibert, B. Dujon. Yeast chromosome XI: construction of a cosmid contig. a high resolution map and sequencing progress. Cold Spring Harbor May 6–10, 1992.

In Preparation

P1. A. Thierry and B. Dujon, Nested Chromosomal Fragmentation Using the Meganuclease I-SceI: Application to the physical mapping of a yeast chromosome and the direct sorting of cosmid libraries. Probably Submission to GENOMICS or EMBO J.

P2. A. Thierry, L. Colleaux and B. Dujon: Construction and Expression of a synthetic gene coding for the meganuclease I-SceI. Possible submission: NAR, EMBO J.

P3. I. Stroke, V. Pelicic and B. Dujon: The evolutionarily conserved dodecapeptide motifs of intron-encoded I-SceI are essential for endonuclease function. Submission to EMBO J.

P4. C. Fairhead and B. Dujon: Consequences of a double strand break induced in vivo in yeast at specific artificial sites, using the meganuclease I-SceI. Possible submission to GENETICS, NATURE.

P5 A. Perrin, and B. Dujon: Asymetrical recognition by the I-SceI endonuclease on exon and intron sequences reveals a new step in intron mobility. Possible submission: NATURE.

The entire disclosure of each of these publications and abstracts is relied upon and incorporated by reference herein.

What is claimed is:

1. An isolated DNA encoding the enzyme I-SceI, wherein the DNA has the nucleotide squence (SEQ ID NO.1):

```
                (SEQ ID NO:1) ATG CAT
                              M   H

ATG AAA AAC ATC AAA AAA AAC CAG GTA ATG  2670
       M   K   N   I   K   K   N   Q   V   M   12

2671 AAC CTC GGT CCG AAC TCT AAA CTG CTG AAA
  13   N   L   G   P   N   S   K   L   L   K

GAA TAC AAA TCC CAG CTG ATC GAA CTG AAC  2730
       E   Y   K   S   Q   L   I   E   L   N   32

2731 ATC GAA CAG TTC GAA GCA GGT ATC GGT CTG
  33   I   E   Q   F   E   A   G   I   G   L

ATC CTG GGT GAT GCT TAC ATC CGT TCT CGT  2790
       I   L   G   D   A   Y   I   R   S   R   52

2791 GAT GAA GGT AAA ACC TAC TGT ATG CAG TTC
  53   D   E   G   K   T   Y   C   M   Q   F

GAG TGG AAA AAC AAA GCA TAC ATG GAC CAC  2850
       E   W   K   N   K   A   Y   M   D   H   72

GTA TGT CTG CTG TAC GAT CAG TGG GTA CTG
  73   V   C   L   L   Y   D   Q   W   V   L

TCC CCG CCG CAC AAA AAA GAA CGT GTT AAC  2910
       S   P   P   H   K   K   E   R   V   N   92

2911 CAC CTG GGT AAC CTG GTA ATC ACC TGG GGC
  93   H   L   G   N   L   V   I   T   W   G

GCC CAG ACT TTC AAA CAC CAA GCT TTC AAC  2970
       A   Q   T   F   K   H   Q   A   F   N   112

2971 AAA CTG GCT AAC CTG TTC ATC GTT AAC AAC
 113   K   L   A   N   L   F   I   V   N   N

AAA AAA ACC ATC CCG AAC AAC CTG GTT GAA  3030
       K   K   T   I   P   N   N   L   V   E   132

3031 AAC TAC CTG ACC CCG ATG TCT CTG GCA TAC
 133   N   Y   L   T   P   M   S   L   A   Y

TGG TTC ATG GAT GAT GGT GGT AAA TGG GAT  3090
       W   F   M   D   D   G   G   K   W   D   152

3091 TAC AAC AAA AAC TCT ACC AAC AAA TCG ATC
 153   Y   N   K   N   S   T   N   K   S   I
```

```
        GTA CTG AAC ACC CAG TCT TTC ACT TTC GAA 3150
        V   L   N   T   Q   S   F   T   F   E   172

3151    GAA GTA GAA TAC CTG GTT AAG GGT CTG CGT
173     E   V   E   Y   L   V   K   G   L   R

AAC AAA TTC CAA CTG AAC TGT TAC GTA AAA 3210
        N   K   F   Q   L   N   C   Y   V   K   192

3211    ATC AAC AAA AAC AAA CCG ATC ATC TAC ATC
193     I   N   K   N   K   P   I   I   Y   I

GAT TCT ATG TCT TAC CTG ATC TTC TAC AAC 3270
        D   S   M   S   Y   L   I   F   Y   N   212

3271    CTG ATC AAA CCG TAC CTG ATC CCG CAG ATG
213     L   I   K   P   Y   L   I   P   Q   M

ATG TAC AAA CTG CCG AAC ACT ATC TCC TCC 3330
        M   Y   K   L   P   N   T   I   S   S   232

3331    GAA ACT TTC CTG AAA TAA
233     E   T   F   L   K   *
```

2. DNA comprising the nucleotide sequence as claimed in claim 1 operatively linked to a promoter.

3. An isolated RNA sequence complementary to the nucleotide sequence of claim 1.

4. RNA complementary to the nucleotide sequence of claim 2.

5. A vehicle comprising a vector containing the nucleotide sequence as claimed in claim 1.

6. The vehicle as claimed in claim 5, wherein the vector is an SV-40 vector.

7. The vehicle as claimed in claim 5, wherein the vector is plasmid pSVOAL.

8. The vehicle as claimed in claim 5 having the identifying characteristics of the vector having culture collection accession number I-1014 in the National Collection of Cultures of Microorganisms.

9. The vehicle as claimed in claim 5, wherein the vector is an expression vector.

10. A process for the expression of a nucleotide sequence encoding the I-SceI enzyme in a host characterized by inserting the nucleotide sequence of claim 1 encoding the I-SceI enzyme in the host, wherein said host is bacteria or a eukaryotic cell.

11. The process of claim 10, wherein said host is bacteria.

12. The process of claim 11, wherein said bacteria is *E. coli*.

13. The process of claim 10, wherein said host is a eukaryotic cell.

14. A process for the production of I-SceI characterized by expressing a vector having the nucleotide sequence of claim 1 in a recombinant host, wherein said host is bacteria or a eukaryotic cell.

15. The process of claim 14, wherein said vector is a plasmid.

16. The process of claim 14, wherein said host is bacteria.

17. The process of claim 16, wherein said bacteria is *E. coli*.

18. The process of claim 14, wherein said host is a eukaryotic cell.

19. A method for in vivo site directed genetic recombination in an organism using enzyme I-SceI, comprising the steps of:

(a) providing an expression vector comprising a synthetic gene encoding I-SceI endonuclease;

(b) providing a plasmid comprising a I-SceI restriction site next to or within a gene of interest carried on said plasmid; (c) co-transforming the cells of said organism with said expression vector of step (a) and said plasmid of step (b); and cleaving said I-SceI restriction site, whereby said cleavage promotes the insertion of said gene of interest into a chromosome of said organism at a specific site by homologous recombination.

20. The method of claim 19, wherein said organism is yeast.

21. The method of claim 19, wherein said organism is bacteria.

22. The method of claim 19, wherein said organism is mouse.

23. The method of claim 19, wherein said synthetic gene of step (a) is under the control of a galactose inducible promoter.

24. The method of claim 23, wherein said expression vector is plasmid pPEX408.

25. The method of claim 23, wherein said expression vector is plasmid pPEX7.

26. The method of claim 19, wherein said cells contain in a chromosome a nucleotide sequence that is homologous to said gene of interest, allowing homogous recombination, and said nucleotide sequence is the specific site of said insertion.

27. A method for in vivo site directed genetic recombination in an organism using enzyme I-SceI, comprising the steps of:

(a) providing a transgenic cell in which at least one I-SceI recognition site is inserted at a unique location in a chromosome;

(b) providing an expression vector comprising a synthetic gene encoding I-SceI endonuclease;

(c) providing a plasmid comprising a gene of interest and a DNA sequence homologous to the sequence of the chromosomal DNA, allowing homologous recombination into which the I-SceI site is inserted;

(d) co-transforming said transgenic cell with said expression vector of step (b) and said plasmid of step (c); and cleaving said I-SceI restriction site, whereby said cleavage promotes the insertion of said gene of interest into said chromosome of said organism at a specific site by homologous recombination.

28. The method of claim 27, wherein said I-SceI restriction site has been introduced into said cells by homologous recombination.

29. The method of claim 27, wherein said I-SceI restriction site has been introduced into said cells by retroviral insertion.

* * * * *